(12) United States Patent
Trieu

(10) Patent No.: US 8,642,060 B2
(45) Date of Patent: *Feb. 4, 2014

(54) CONTROLLED RELEASE SYSTEMS AND METHODS FOR OSTEAL GROWTH

(75) Inventor: Hai H. Trieu, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1830 days.

This patent is subject to a terminal disclaimer.

(21) Appl. No.: 11/517,693

(22) Filed: Sep. 8, 2006

(65) Prior Publication Data

US 2007/0250045 A1    Oct. 25, 2007

Related U.S. Application Data

(63) Continuation-in-part of application No. 11/410,216, filed on Apr. 24, 2006.

(51) Int. Cl.
*A61B 17/56* (2006.01)
*A61F 17/00* (2006.01)
*A61K 9/22* (2006.01)
*A61F 2/44* (2006.01)

(52) U.S. Cl.
USPC ..... 424/422; 424/423; 604/890.1; 604/891.1; 604/892.1; 623/17.12

(58) Field of Classification Search
USPC ......... 424/422, 423; 604/890.1, 891.1, 892.1; 623/17.12
See application file for complete search history.

(56) References Cited

U.S. PATENT DOCUMENTS

| | | | |
|---|---|---|---|
| 3,320,131 A | 5/1967 | Smith | |
| 3,941,127 A | 3/1976 | Froning | |
| 3,964,480 A | 6/1976 | Froning | |
| 4,039,682 A | 8/1977 | Ausman et al. | |
| 4,374,926 A | 2/1983 | Stern | |
| 4,430,760 A | 2/1984 | Smestad | |
| 4,439,423 A | 3/1984 | Smith | |
| 4,696,816 A | 9/1987 | Brown | |
| 4,719,108 A | 1/1988 | Smith | |
| 4,904,260 A | 2/1990 | Ray et al. | |
| 5,422,103 A | 6/1995 | Stern et al. | |
| 5,456,679 A | 10/1995 | Balaban et al. | |
| 5,468,480 A | 11/1995 | Barrett et al. | |
| 5,645,549 A | 7/1997 | Boyd et al. | |
| 5,919,235 A | 7/1999 | Husson et al. | |
| 6,007,810 A | 12/1999 | Ishikawa et al. | |
| 6,063,378 A | 5/2000 | Nohara et al. | |
| 6,231,615 B1 | 5/2001 | Preissman | |
| 6,280,475 B1 | 8/2001 | Bao et al. | |
| 6,294,187 B1 | 9/2001 | Boyce et al. | |
| 6,471,688 B1 | 10/2002 | Harper et al. | |
| 6,491,666 B1 | 12/2002 | Santini, Jr. et al. | |
| 6,527,762 B1 | 3/2003 | Santini, Jr. et al. | |
| 6,537,256 B2 | 3/2003 | Santini, Jr. et al. | |
| 6,551,838 B2 | 4/2003 | Santini, Jr. et al. | |
| 6,656,162 B2 | 12/2003 | Santini, Jr. et al. | |
| 6,669,683 B2 | 12/2003 | Santini, Jr. et al. | |
| 6,773,429 B2 | 8/2004 | Sheppard, Jr. et al. | |
| 6,827,250 B2 | 12/2004 | Uhland et al. | |
| 6,849,463 B2 | 2/2005 | Santini, Jr. et al. | |
| 6,973,718 B2 | 12/2005 | Sheppard, Jr. et al. | |
| 6,976,982 B2 | 12/2005 | Santini, Jr. et al. | |
| 7,014,636 B2 | 3/2006 | Gilbert | |
| 7,163,545 B2 | 1/2007 | Yazemski et al. | |
| 7,217,293 B2 * | 5/2007 | Branch, Jr. | 623/17.16 |
| 2001/0020188 A1 | 9/2001 | Sander | |
| 2002/0026244 A1 | 2/2002 | Trieu | |
| 2002/0029083 A1 | 3/2002 | Zucherman et al. | |
| 2002/0087113 A1 * | 7/2002 | Hartlaub | 604/65 |
| 2002/0128202 A1 | 9/2002 | Carney et al. | |
| 2002/0173851 A1 | 11/2002 | McKay | |
| 2003/0009235 A1 | 1/2003 | Manrique et al. | |
| 2003/0039676 A1 | 2/2003 | Boyce et al. | |
| 2004/0031666 A1 * | 2/2004 | Ostman | 198/836.1 |
| 2004/0091540 A1 | 5/2004 | Desrosiers et al. | |
| 2004/0121486 A1 | 6/2004 | Uhland et al. | |
| 2004/0133280 A1 | 7/2004 | Trieu | |
| 2004/0143242 A1 * | 7/2004 | Ludin et al. | 604/891.1 |
| 2004/0220552 A1 | 11/2004 | Heruth et al. | |
| 2005/0031666 A1 * | 2/2005 | Trieu | 424/426 |
| 2005/0070778 A1 * | 3/2005 | Lackey et al. | 600/366 |
| 2005/0071009 A1 | 3/2005 | Mahanna et al. | |
| 2006/0004456 A1 | 1/2006 | McKay | |

(Continued)

FOREIGN PATENT DOCUMENTS

WO    9634093    10/1996
WO    0145577 A3    6/2001

(Continued)

OTHER PUBLICATIONS

Gunter et al, Hydration Level Monitoring Using Embedded Piezoresistive Microcantilever Sensors, Medical Engineering & Physics 27 (2005) 215-220.*

(Continued)

*Primary Examiner* — Blessing M Fubara
*Assistant Examiner* — Kauser M Akhoon
(74) *Attorney, Agent, or Firm* — Sorell Lenna & Schmidt LLP

(57) ABSTRACT

A device includes a first reservoir configured to include a degradation agent, a second reservoir configured to include an osteogenerative agent, and a controller configured to selectively initiate access to the first reservoir or the second reservoir.

17 Claims, 19 Drawing Sheets

(56) References Cited

U.S. PATENT DOCUMENTS

| | | |
|---|---|---|
| 2006/0046961 A1 | 3/2006 | McKay et al. |
| 2006/0047341 A1 | 3/2006 | Trieu |
| 2007/0003598 A1 | 1/2007 | Trieu |
| 2007/0250044 A1 | 10/2007 | Trieu |
| 2007/0250045 A1 | 10/2007 | Trieu |
| 2007/0250046 A1 | 10/2007 | Trieu |
| 2007/0276337 A1 | 11/2007 | Trieu |

FOREIGN PATENT DOCUMENTS

| | | |
|---|---|---|
| WO | 0217824 A3 | 3/2002 |
| WO | 03068149 A3 | 8/2003 |
| WO | 2004047691 A | 6/2004 |
| WO | 2004101015 A2 | 11/2004 |
| WO | 2005065079 A2 | 7/2005 |
| WO | 2005092249 A1 | 10/2005 |
| WO | 2005102440 A2 | 11/2005 |
| WO | 2005115438 A1 | 12/2005 |
| WO | 2006017456 A2 | 2/2006 |
| WO | 2006050106 A | 5/2006 |
| WO | 2006055547 A | 5/2006 |
| WO | 2007127548 A | 11/2007 |
| WO | 2008030832 A1 | 3/2008 |
| WO | 2008030963 A1 | 3/2008 |

OTHER PUBLICATIONS

Sheikh H et al. 2009. In vivo intervertebral disc regeneration using stem cell-derived chondroprogenitors. J Neurosurg Spine 10: 265-272.

Bron JL et al. 2009. Repair, regenerative and supportive therapies of the annulus fibrosus: achievements and challenges. Eur Spine J 18:301-313.

Chymopapain from GenBank Accession No. CAA66378, pp. 1-2. Accessed May 14, 2009.

Collagenase from GenBank Accession No. CAA07432, pp. 1-3. Accessed May 14, 2009.

Fibroblast growth factor from GenBank Accession No. CAA41788, pp. 1-2. Accessed May 14, 2009.

Morphogenetic protein from GenBank Accession No. NP_391488, pp. 1-3. Accessed May 14, 2009.

Albumin from GenBank Accession No. CAA00606, pp. 1-2. Accessed May 14, 2009.

* cited by examiner

CONTROLLED RELEASE SYSTEMS AND METHODS FOR OSTEAL GROWTH

CROSS-REFERENCE TO RELATED APPLICATION(S)

This application is a continuation-in-part and claims priority to U.S. application Ser. No. 11/410,216, entitled "CONTROLLED RELEASE SYSTEMS AND METHODS FOR INTERVERTEBRAL DISCS," filed Apr. 24, 2006, and naming inventor Hai H. Trieu, which is incorporated herein by reference in its entirety.

FIELD OF THE DISCLOSURE

The present disclosure relates generally to controlled release devices. More specifically, the present disclosure relates to controlled release devices for implanting in a soft tissue adjacent an osteal structure.

BACKGROUND

In human anatomy, the spine is a generally flexible column that can withstand tensile and compressive loads. The spine also allows bending motion and provides a place of attachment for keels, muscles, and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Three joints reside between each set of two vertebrae: a larger intervertebral disc between the two vertebral bodies and two zygapophyseal joints located posteriolaterally relative to the vertebral bodies and between opposing articular processes.

The intervertebral discs generally function as shock absorbers and as joints. Further, the intervertebral discs can absorb the compressive and tensile loads to which the spinal column can be subjected. At the same time, the intervertebral discs can allow adjacent vertebral bodies to move relative to each other, particularly during bending or flexure of the spine. Thus, the intervertebral discs are under constant muscular and gravitational pressure and generally, the intervertebral discs are the first parts of the lumbar spine to show signs of deterioration.

The zygapophyseal joints permit movement in the vertical direction, while limiting rotational motion of two adjoining vertebrae. In addition, capsular ligaments surround the zygapophyseal joints, discouraging excess extension and torsion. In addition to intervertebral disc degradation, zygapophyseal joint degeneration is also common because the zygapophyseal joints are in almost constant motion with the spine. In fact, zygapophyseal joint degeneration and disc degeneration frequently occur together. Generally, although one can be the primary problem while the other is a secondary problem resulting from the altered mechanics of the spine, by the time surgical options are considered, both zygapophyseal joint degeneration and disc degeneration typically have occurred. For example, the altered mechanics of the zygapophyseal joints or the intervertebral disc can cause spinal stenosis, degenerative spondylolisthesis, and degenerative scoliosis.

Furthermore, acute strenuous events, such as whiplash or overextension, can damage capsular ligaments. Such damage to capsular ligaments if untreated can lead to degradation of the zygapophyseal joint or of the intervertebral disc.

In particular, deterioration can be manifested as a herniated disc. Weakness in an annulus fibrosis can result in a bulging of the nucleus pulposus or a herniation of the nucleus pulposus through the annulus fibrosis. Ultimately, weakness of the annulus fibrosis can result in a tear, permitting the nucleus pulposus to leak from the intervertebral space. Loss of the nucleus pulposus or a bulging of the nucleus pulposus can lead to pinching of nerves, causing pain and damage to vertebrae. In addition, aging can lead to a reduction in the hydration of the nucleus pulposus. Such a loss in hydration can also result in pinching of nerves.

A traditional option for treating a patient includes replacement of the intervertebral disc or the zygapophyseal joint with an implant. Another traditional option includes fusing adjacent vertebra using fasteners, such as traditional screws or rods. However, such traditional methods are typically implemented with invasive surgical procedures. In particular, some traditional surgical procedures access the spine through the abdominal cavity, introducing risk to major organs and often leaving large scars.

DESCRIPTION OF DRAWINGS

In a particular embodiment, a controlled release device includes a reservoir configured to store a degradation agent, a reservoir configured to store an osteogenerative agent, and a controller. The degradation agent can influence a condition of a soft tissue, such as a nucleus pulposus or a zygapophyseal joint. For example, the degradation agent can be a nucleolytic agent configured to deconstruct the soft tissue. The controlled release device is configured to selectively release the degradation agent or the osteogenerative agent, such as in response to a signal received from a sensor. In a particular example, the controller receives a signal from the sensor indicative of a condition of the nucleus pulposus and selectively releases the agent to effect the bone growth.

In an embodiment, a device includes a first reservoir configured to include a degradation agent, a second reservoir configured to include an osteogenerative agent, and a controller configured to selectively initiate access to the first reservoir or the second reservoir.

In another exemplary embodiment, an implantable medical device includes a first reservoir configured to include a degradation agent, a second reservoir configured to include an osteogenerative agent, and a controller configured to initiate release of the degradation agent from the first reservoir prior to initiating release of the osteogenerative agent from the second reservoir.

In a further exemplary embodiment, an implantable medical device includes a first reservoir configured to include a degradation agent, a second reservoir configured to include an osteogenerative agent, a sensor configured to sense a condition of a soft tissue, and a controller in communication with the sensor. The controller is configured to selectively initiate access to the first reservoir or to the second reservoir based on a signal from the sensor.

In an additional embodiment, a method of treating a patient includes inserting an implantable device into a soft tissue adjacent an osteal structure. The implantable device includes a first reservoir configured to include a degradation agent, a second reservoir configured to include an osteogenerative agent, and a controller configured to selectively initiate access to the first reservoir or the second reservoir.

In another exemplary embodiment, a method of treating a patient includes sensing a condition of a soft tissue with a sensor of a medical device implanted at least partially in the soft tissue, and selectively releasing a degradation agent or an osteogenerative agent from the medical device based on a signal from the sensor.

Description of Relevant Anatomy

Figure 1:
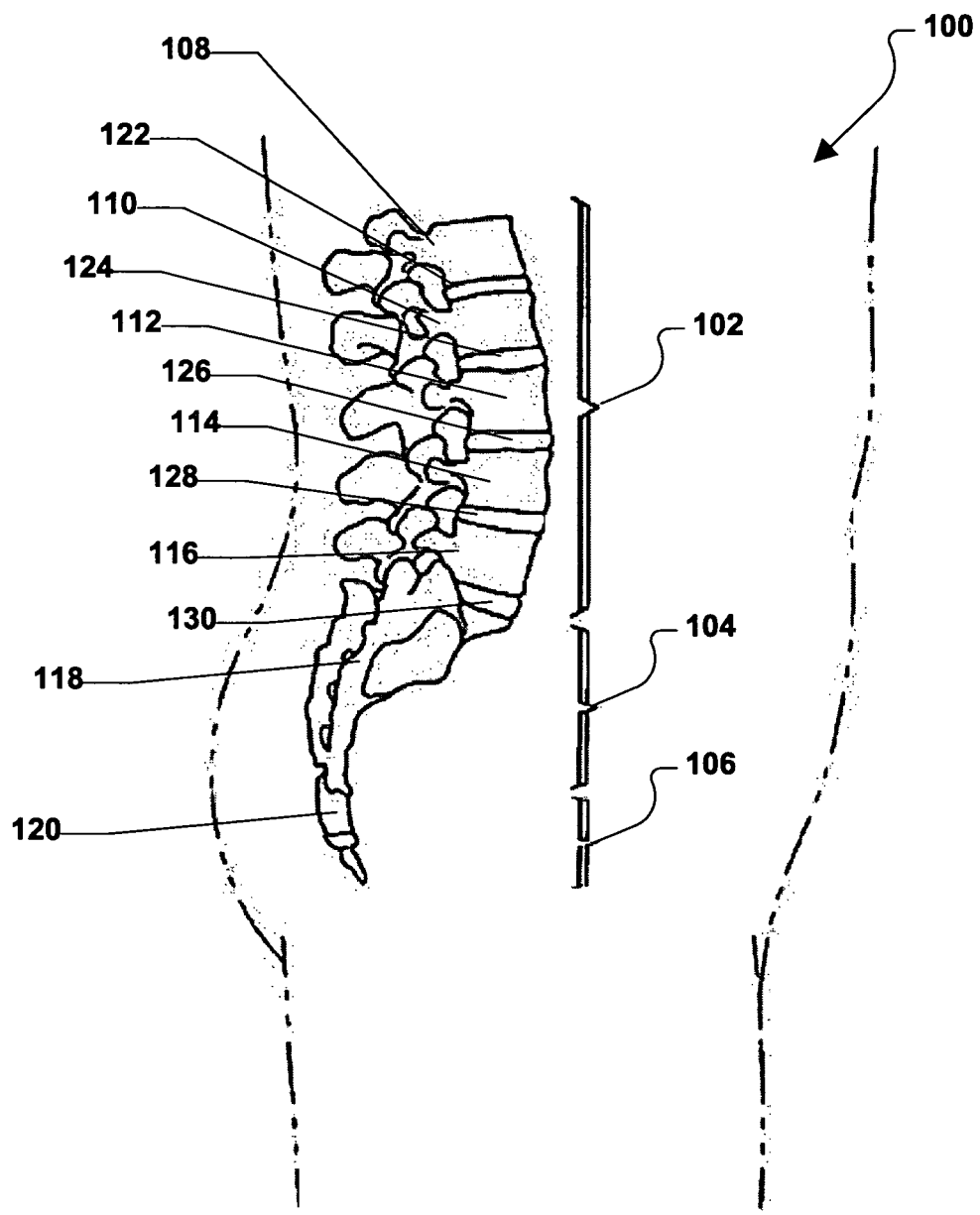
FIG. 1 includes a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, or damaged or if one of the zygapophyseal joints is diseased, degenerated or damaged, that disc or joint can be at least partially treated with an implanted device according to one or more of the embodiments described herein. In a particular embodiment, a controlled release device can be inserted into the intervertebral lumbar disc 122, 124, 126, 128, 130 or a zygapophyseal joint.

Figure 2:
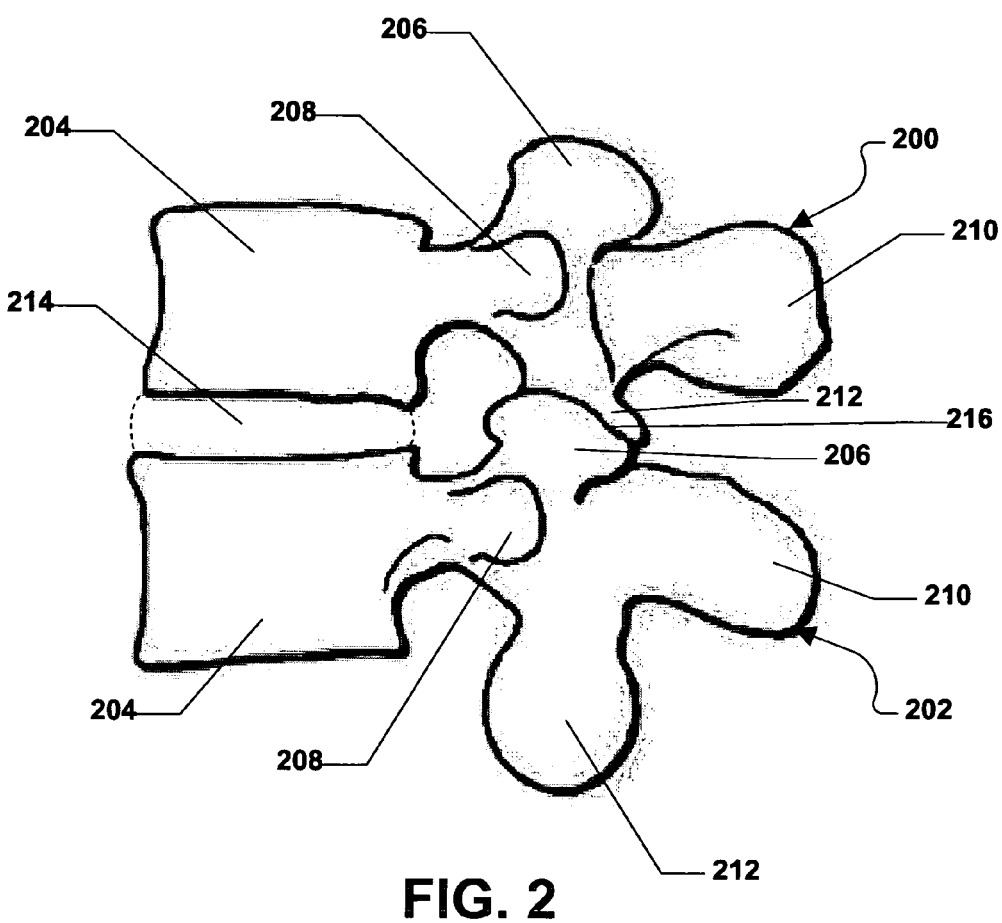
FIG. 2 includes a lateral view of a pair of adjacent vertebrae.

FIG. 2 depicts a detailed lateral view of two adjacent vertebrae, e.g., two of the lumbar vertebrae 108, 110, 112, 114, 116 illustrated in FIG. 1. FIG. 2 illustrates a superior vertebra 200 and an inferior vertebra 202. As illustrated, each vertebra 200, 202 includes a vertebral body 204, a superior articular process 206, a transverse process 208, a spinous process 210 and an inferior articular process 212. FIG. 2 further depicts an intervertebral disc 214 between the superior vertebra 200 and the inferior vertebra 202. A zygapophyseal joint 216 is located between the inferior articular process 212 of the superior vertebra 200 and the superior articular process 206 of the inferior vertebra 202. As described in greater detail below, an intervertebral controlled release device according to one or more of the embodiments described herein can be installed within or in proximity to the intervertebral disc 214 between the superior vertebra 200 and the inferior vertebra 202 or within or in proximity to the zygapophyseal joint 216.

Figure 3:
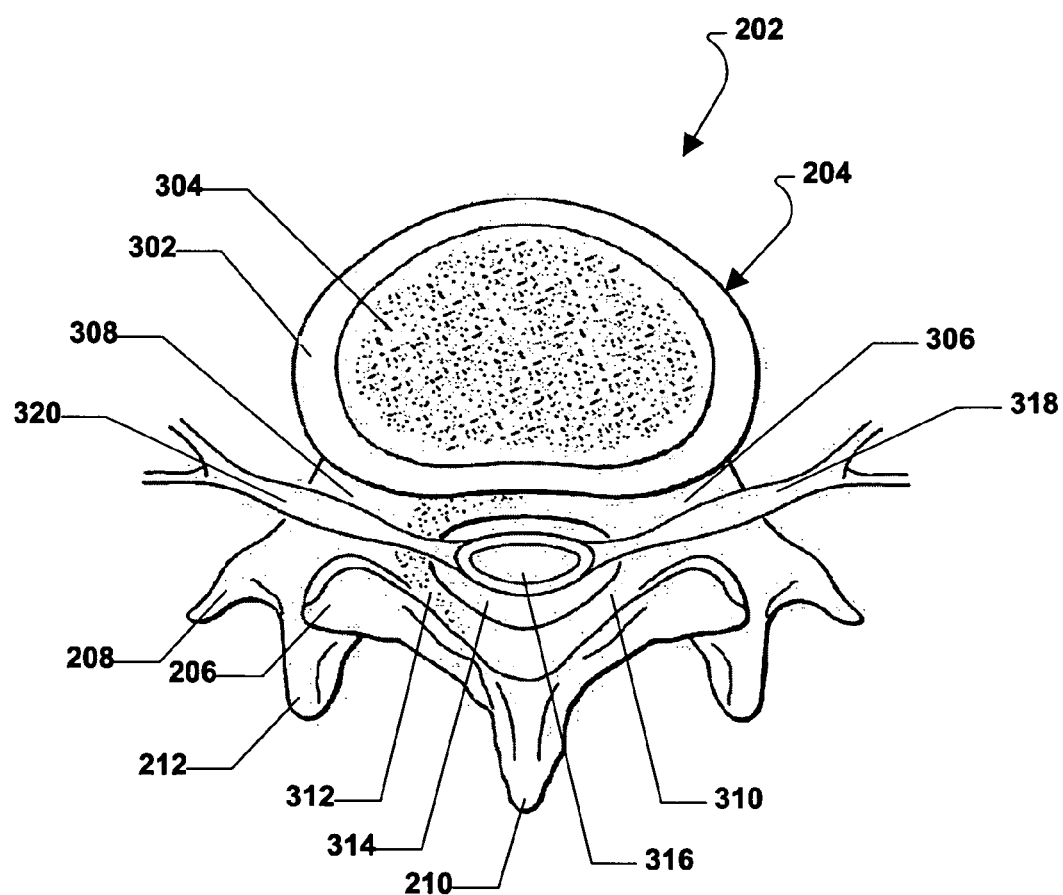
FIG. 3 includes a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is generally softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
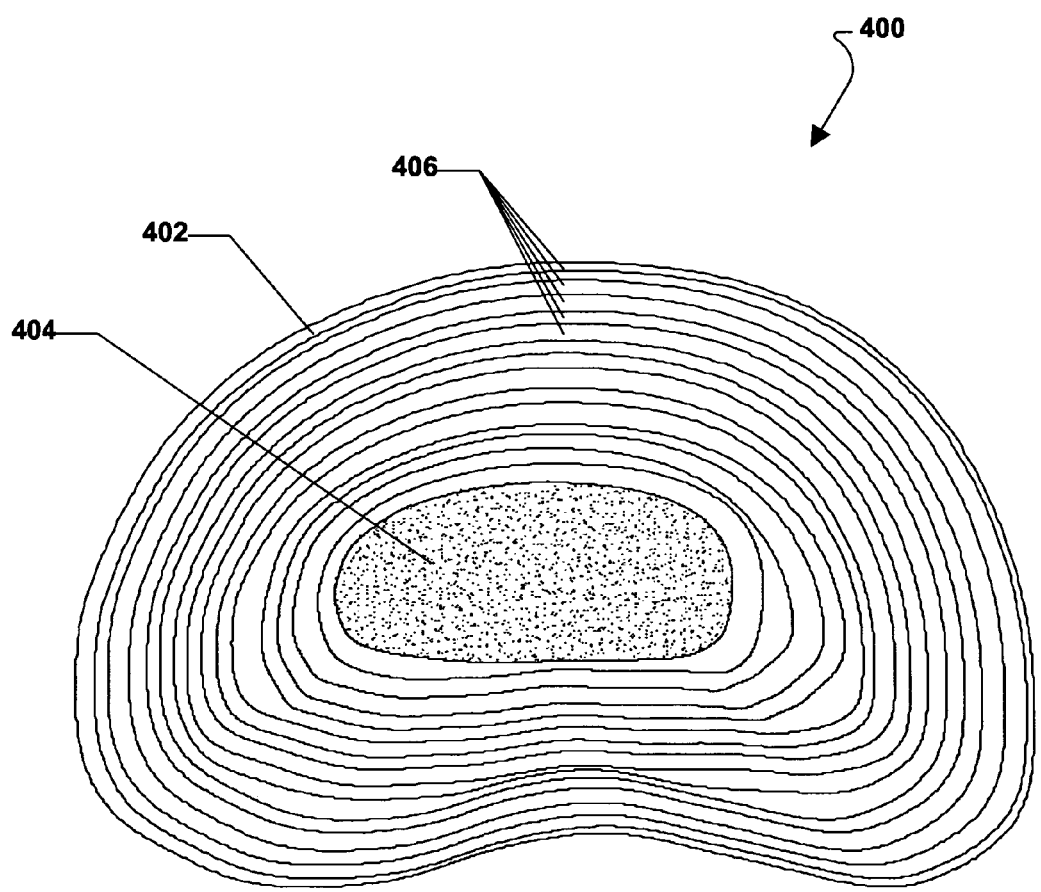
FIG. 4 includes a cross section view of an intervertebral disc.

Referring now to FIG. 4, an intervertebral disc is shown and is generally designated 400. The intervertebral disc 400 is made up of two components: an annulus fibrosis 402 and a nucleus pulposus 404. The annulus fibrosis 402 is the outer portion of the intervertebral disc 400, and the annulus fibrosis 402 includes a plurality of lamellae 406. The lamellae 406 are layers of collagen and proteins. Each lamella 406 includes fibers that slant at 30-degree angles, and the fibers of each lamella 406 run in a direction opposite the adjacent layers. Accordingly, the annulus fibrosis 402 is a structure that is exceptionally strong, yet extremely flexible.

The nucleus pulposus 404 is an inner gel material that is surrounded by the annulus fibrosis 402. It makes up about forty percent (40%) of the intervertebral disc 400 by weight. Moreover, the nucleus pulposus 404 can be considered a ball-like gel that is contained within the lamellae 406. The nucleus pulposus 404 includes loose collagen fibers, water, and proteins. The water content of the nucleus pulposus 404 is about ninety percent (90%) by weight at birth and decreases to about seventy percent by weight (70%) by the fifth decade.

Injury or aging of the annulus fibrosis 402 can allow the nucleus pulposus 404 to be squeezed through the annulus fibers either partially, causing the disc to bulge, or completely, allowing the disc material to escape the intervertebral disc 400. The bulging disc or nucleus material can compress the nerves or spinal cord, causing pain. Accordingly, the nucleus pulposus 404 can be treated with an implantable controlled release device to treat the intervertebral disc 400.

Figure 5:
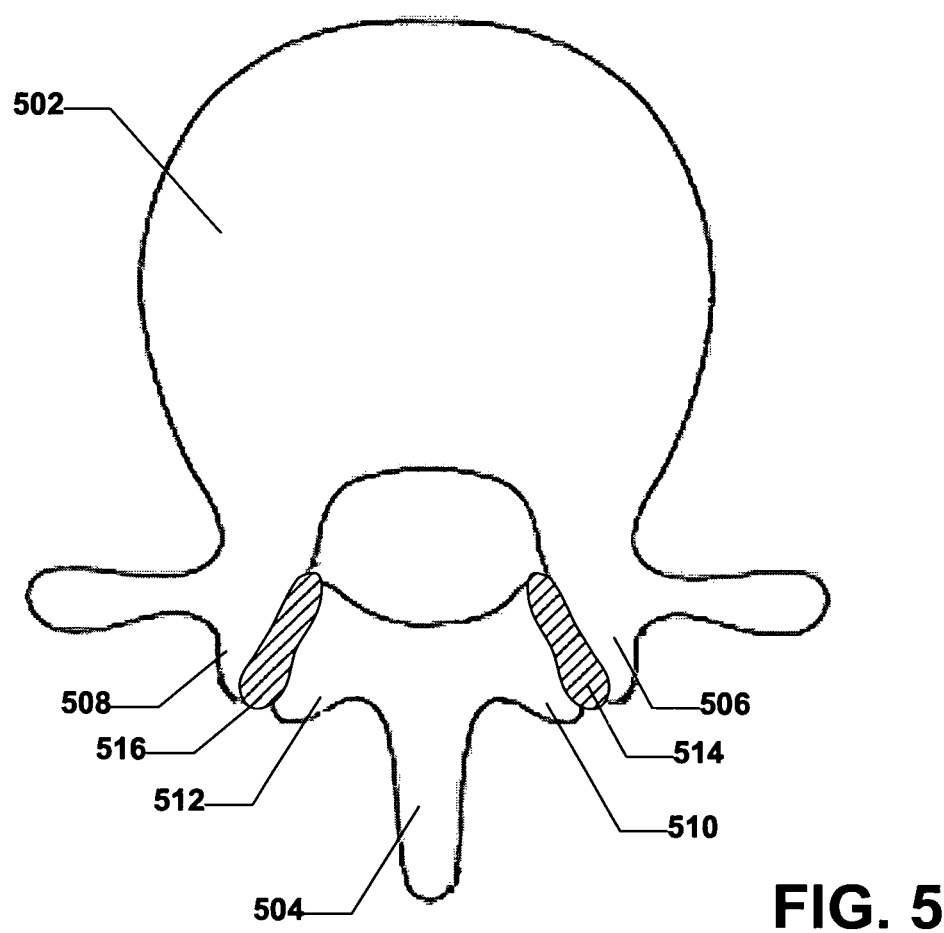
FIG. 5 includes a cross section view of a zygapophyseal joint.

FIG. 5 includes a cross-sectional view of the spine illustrating a portion of a superior vertebra 504 and a portion of an inferior vertebra 502. The inferior vertebra 502 includes superior articular processes 506 and 508 and the superior vertebra 504 includes inferior articular processes 510 and 512. Between the superior articular process 506 and the inferior articular process 510 is a zygapophyseal joint 514 and between the superior articular process 508 and the inferior articular process 512 is a zygapophyseal joint 516.

When damaged or degraded, the zygapophyseal joints 514 and 516 can be treated. For example, an implantable device can be inserted into or in proximity to the zygapophyseal joints 514 and 516. In particular, such an implantable device can be configured to fuse the inferior articular process (506 or 508) to the superior articular process (510 or 512).

Description of Agents

In an exemplary embodiment, a device to be implanted at least partially in the nucleus pulposus of an intervertebral disc or in a zygapophyseal joint includes at least one reservoir to store an agent. The agent can generally affect a condition of the nucleus pulposus or affect bone growth. For example, the agent can decrease the hydration level of the nucleus pulposus or can cause a degeneration of the nucleus pulposus that leads to a reduction in hydration level, to a reduction in pressure, or to a reduction in size of the nucleus pulposus within the intervertebral disc. An agent causing a degeneration of the disc or reduction in hydration level is herein termed a "degradation agent." In another example, an agent (e.g., an osteogenerative agent) can affect bone growth in proximity to the intervertebral disc or the zygapophyseal joint. For example, an osteogenerative agent can be an osteoinductive agent, an osteoconductive agent, or any combination thereof.

An exemplary degradation agent can reduce hydration levels in the nucleus pulposus or can degrade the nucleus pulposus, resulting in a reduction in hydration level or in pressure within the intervertebral disc. For example, the degradation agent can be a nucleolytic agent that acts on portions of the nucleus pulposus. In an example, the nucleolytic agent is proteolytic, breaking down proteins.

An exemplary nucleolytic agent includes a chemonucleolysis agent, such as chymopapain, collagenase, chondroitinase, keratanase, human proteolytic enzymes, papaya proteinase, or any combination thereof. An exemplary chondroitinase can include chondroitinase ABC, chondroitinase AC, chondroitinase ACII, chondroitinase ACIII, chondroitinase B, chondroitinase C, or the like, or any combination thereof. In another example, a keratanase can include endo-β-galactosidase derived from *Escherichia freundii*, endo-β-galactosidase derived from *Pseudomonas* sp. IFO-13309 strain, endo-β-galactosidase produced by *Pseudomonas reptilivora*, endo-β-N-acetylglucosaminidase derived from *Bacillus* sp. Ks36, endo-β-N-acetylglucosaminidase derived from *Bacillus circulans* KsT202, or the like, or any combination thereof. In a particular example, the degradation agent includes chymopapain. In another example, the degradation agent includes chondroitinase-ABC.

An osteogenerative agent, for example, can encourage the formation of new bone ("osteogenesis"), such as through inducing bone growth ("osteoinductivity") or by providing a structure onto which bone can grow ("osteoconductivity"). Generally, osteoconductivity refers to structures supporting the attachment of new osteoblasts and osteoprogenitor cells. As such, the agent can form an interconnected structure through which new cells can migrate and new vessels can form. Osteoinductivity typically refers to the ability of the implantable device or a surface or a portion thereof to induce nondifferentiated stem cells or osteoprogenitor cells to differentiate into osteoblasts.

In an example, an osteoconductive agent can provide a favorable scaffolding for vascular ingress, cellular infiltration and attachment, cartilage formation, calcified tissue deposition, or any combination thereof. An exemplary osteoconductive agent includes collagen; a calcium phosphate, such as hydroxyapatite, tricalcium phosphate, or fluorapatite; calcium sulfate; demineralized bone matrix; or any combination thereof.

In another example, an osteoinductive agent can include bone morphogenetic proteins (BMP, e.g., rhBMP-2); demineralized bone matrix; transforming growth factors (TGF, e.g., TGF-β); osteoblast cells, growth and differentiation factor (GDF), LIM mineralized protein (LMP), platelet derived growth factor (PDGF), insulin-like growth factor (ILGF), fibroblast growth factor (FGF), platelet derived growth factor (PDGF), members of the hedgehog family of proteins, interleukins (Ils), colony stimulating factors (CSF), cartilage derived growth factors (CDGF), cartilage derived morphogenetic proteins (CDMP), or any combination thereof. In a further example, an osteoinductive agent can include HMG-CoA reductase inhibitors, such as a member of the statin family, such as lovastatin, simvastatin, pravastatin, fluvastatin, atorvastatin, cerivastatin, mevastatin, pharmaceutically acceptable salts esters or lactones thereof, or any combination thereof. With regard to lovastatin, the substance can be either the acid form or the lactone form or a combination of both. In a particular example, the osteoinductive agent includes a growth factor. In addition, osteoconductive and osteoinductive properties can be provided by bone marrow, blood plasma, or morselized bone of the patient, or other commercially available materials.

In addition, the implantable device can include an anti-inflammatory agent. An exemplary anti-inflammatory agent can include a soluble tumor necrosis factor α-receptor, a pegylated soluble tumor necrosis factor α-receptor, a monoclonal antibody, a polyclonal antibody, an antibody fragment, a COX-2 inhibitor, a metalloprotease inhibitor, a glutamate antagonist, a glial cell derived neurotrophic factor, a B2 receptor antagonist, a substance P receptor (NK1) antagonist, a downstream regulatory element antagonistic modulator (DREAM), iNOS, an inhibitor of tetrodotoxin (TTX)-resistant Na+-channel receptor subtypes PN3 and SNS2, an inhibitor of interleukin, a TNF binding protein, a dominant-negative TNF variant, Nanobodies™, a kinase inhibitor, or any combination thereof. Another exemplary anti-inflammatory agent can include Adalimumab, Infliximab, Etanercept, Pegsunercept (PEG sTNF-R1), Onercept, Kineret®, sTNF-R1, CDP-870, CDP-571, CNI-1493, RDP58, ISIS 104838, 1→3-β-D-glucan, Lenercept, PEG-sTNFRII Fc Mutein, D2E7, Afelimomab, AMG 108, 6-methoxy-2-napthylacetic acid or betamethasone, capsaiein, civanide, TNFRc, ISIS2302 and GI 129471, integrin antagonist, alpha-4 beta-7 integrin antagonist, cell adhesion inhibitor, interferon gamma antagonist, CTLA4-Ig agonist/antagonist (BMS-188667), CD40 ligand antagonist, Humanized anti-IL-6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-10, HuMax IL-15 (anti-IL 15 antibody), or any combination thereof.

In addition, other agents can be incorporated into a reservoir, such as an antibiotic, an analgesic, an anesthetic, a radiographic agent, or any combination thereof. For example, a pain medication can be incorporated within the reservoir in which another agent is contained or in a separate reservoir. An exemplary pain medication includes codeine, propoxyphene, hydrocodone, oxycodone, or any combination thereof. In a further example, an antiseptic agent can be incorporated within a reservoir. For example, the antiseptic agent can include an antibiotic agent. In an additional example, a radiographic agent can be incorporated into a reservoir, such as an agent responsive to x-rays.

Each of the agents or a combination of agents can be maintained in liquid, gel, paste, slurry, solid form, or any combination thereof. Solid forms include powder, granules, microspheres, miniature rods, or embedded in a matrix or binder material, or any combination thereof. In an example, fluids or water from surrounding tissues can be absorbed by the device and placed in contact with an agent in solid form prior to release. Further, a stabilizer or a preservative can be included with the agent to prolong activity of the agent.

In particular, one or more agents can be incorporated into a polymeric matrix, such as a hydrogel, a bioresorbable polymer, or a natural polymer. An exemplary hydrogel can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or any combination thereof. An exemplary bioresorbable polymer can include polylactide (PLA), polyglycolide (PGA), poly(lactide-co-glycolide) (PLGA), polyanhydride, polyorthoester, or any combination thereof. An exemplary natural polymer can include a polysaccharide, collagen, silk, elastin, keratin, albumin, fibrin, starch, chitosans, gelatin, alginates, dextrans, or any combination thereof. Other exemplary polymers include poly(alpha-hydroxy acids), conjugates of poly(alpha-hydroxy acids), polyaspirins, polyphosphagenes, PVA-g-PLGA, PEGT-PBT copolymer (polyactive), PEO-PPO-PEO (pluronics), PEO-PPO-PAA copolymers, PLGA-PEO-PLGA, polyphosphoesters, polyester-anhydrides, polyamino acids, polyurethane-esters, polyphosphazines, polycaprolactones, polytrimethylene carbonates, polydioxanones, polyamide-esters, polyketals, polyacetals, glycosaminoglycans, hyaluronic acid, hyaluronic acid esters, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyethylene oxides, polyorthocarbonates, polycarbonates, or copolymers or physical blends thereof or combinations thereof.

Description of a Device

In a embodiment, an implantable device can include a reservoir configured to store a degradation agent and a reservoir configured to store an osteogenerative agent. In addition, the device can include a controller to initiate release of the degradation agent or the osteogenerative agent, such as through initiating access to one of the reservoirs. In a particular example illustrated in FIG. 8, the implantable device 800 can be configured to release at least a portion of the degradation agent prior to releasing the osteogenerative agent. For example, the implantable device 800 can be configured to release the degradation agent after implantation of the implantable device 800 into a soft tissue and the controller 802 can be configured to initiate release of the osteogenerative agent after a period of time or when a condition is met.

In addition, the implantable device 800 can include a sensor 813 in communication with the controller 802. The sensor 813 can measure conditions associated with the soft tissue. For example, the sensor 813 can measure a condition, such as hydration level, pressure, pH, electrolyte levels, or analyte levels. In particular, a sensor 813 can be configured to measure a level of an analyte indicative of the state of the soft tissue, such as degradation byproducts, degradation reactionary products, cytokines, or any combination thereof.

Based at least in part on a signal from the sensor 813, the implantable device 800 can be configured to initiate release of the degradation agent or the osteogenerative agent. In particular, the controller 802 can respond to a signal from the sensor 813 to initiate the release of an agent. For example, the controller 802 can initiate the release of an agent based on an average pressure associated with the soft tissue or based on a hydration level of the soft tissue.

Figure 6:
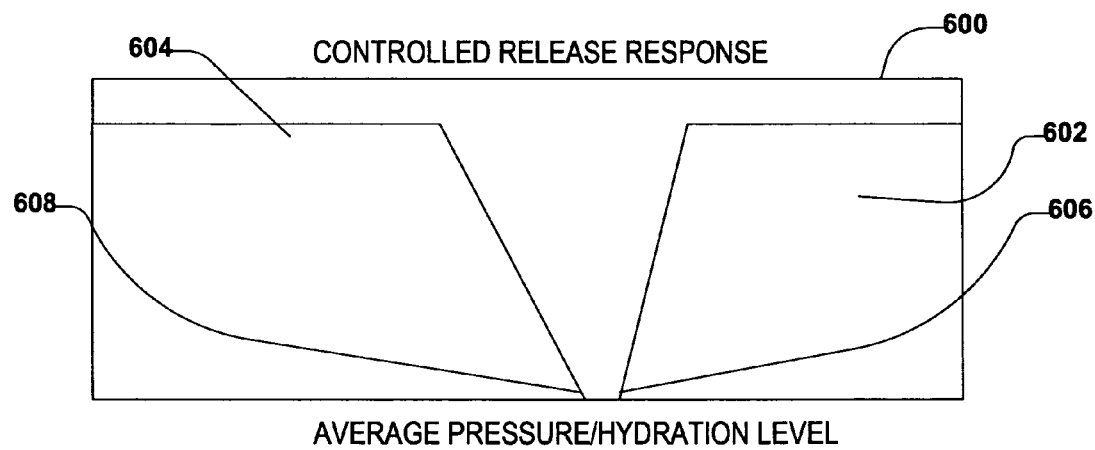
FIG. 6 and FIG. 7 include graphical representations of exemplary control strategies.

In particular, FIG. 6 includes an illustration of an exemplary control strategy 600. For example, when the hydration level is above a threshold 606, the implantable device can be configured to release a degradation agent, as indicated by the release profile 602. In particular, when the hydration level or average pressure indicates the presence of tissue, such as a nucleus pulposus, the controller can be configured to release degradation agent. Typically, as the quality and quantity of soft tissue in an intervertebral disc or a zygapophyseal joint decreases, the hydration level or the average pressure of the soft tissue decreases. In addition, when the hydration level or the average pressure decreases below a particular threshold 608, the implantable device can be configured to release an osteogenerative agent, as indicated by the release profile 604.

Figure 7:
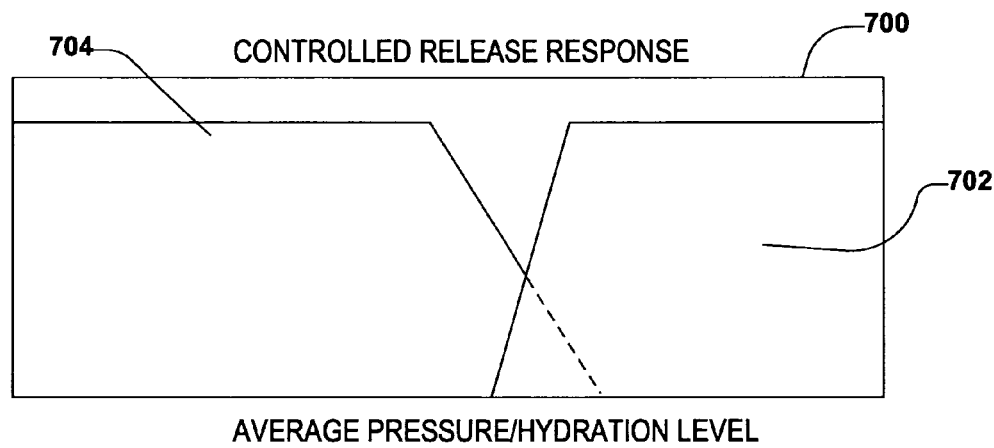

In a further exemplary control strategy 700 illustrated in FIG. 7, the release profile 702 of the degradation agent can overlap with the release profile 704 of the osteogenerative agent. For example, as a sensor indicates degradation of a soft tissue, the controller can be configured to initiate release of an osteogenerative agent.

While the control strategies illustrated in FIG. 6 and FIG. 7 rely on average pressure or hydration level, other conditions can be used as the basis of a controlled release response. Further, other control strategies, such as timed release, feedback control (e.g., proportional, integral or differential (PID) control), and model-based control, can be used in conjunction with an implantable device.

Returning to FIG. 8, various control strategies can be implemented by an implantable device 800 that can include a sensor 813, a controller 802, and a reservoir 804 to store an agent. The exemplary device 800 includes a controller 802. A sensor, such as the sensors 813 and 814, can be in communication with the controller 802. In addition, the device 800 can include a reservoir, such as the reservoirs 804 and 806. The controller 802 can be communicatively coupled to a control element, such as the control elements 808 and 810, associated with the reservoir, such as the reservoirs 804 and 806, respectively. In addition, the controller 802 can be communicatively coupled to a reservoir driver 812 that can motivate movement of an agent from the reservoir, such as the reservoirs 804 and 806.

In an exemplary embodiment, the controller 802 can receive a signal from the sensor (813 or 814) and in response, manipulate the control element (808 or 810). For example, the controller 802 can include control circuitry, such as an algorithmic or arithmetic control circuitry. In an example, the controller 802 includes a proportional, integral, or differential (PID) controller. Alternatively, the controller 802 can include a processor configured to receive sensor data, such as data from the sensors 813 or 814, and determine a dosage to be delivered or a release response. Based on the dosage or the release response, the processor can manipulate the control elements 808 or 810 or the reservoir driver 812. For example, the controller 802 can apply sensor data to an algorithm, an arithmetic model, an artificial intelligence engine, a threshold, or any combination thereof to determine a dosage or a control protocol. An exemplary artificial intelligence engine includes a neural network, a fuzzy logic engine, a complex control model, or any combination thereof. In a further example, the controller 802 can perform calculations using the sensor data to determine, for example, a time average, a minimum value, a maximum value, a median value, a rate of change, a trend, or any combination thereof. Further, measurements can be selected or selectively weighted based on the time of day in which taken. For example, pressure data measured at a time at which a patient is typically asleep can be selected in contrast to pressure data measured during periods of high activity.

In an exemplary embodiment, the device 800 includes one or more sensors, such as sensors 813 or 814. An exemplary sensor (813 or 814) can include a pressure transducer, a moisture or hydration sensor, a pH sensor, a resistance or conductance meter, an electrolyte detector, a force sensor, a stress sensor, a relative motion sensor, or any combination thereof. In a particular example, the sensor (813 or 814) can sense the relative motion of two osteal structures, such as a superior and an inferior vertebrae. In another example, one or more sensors can be provided to sense different degradation products. Based on signals produced by the one or more sensors (813 or 814), the controller 802 can selectively initiate the release of an agent. In addition, the controller 802 can store sensor data in a memory 816.

The device 800 can also include one or more reservoirs, such as reservoirs 804 or 806. The reservoir (804 or 806) can include an agent, such as an osteogenerative agent or a degradation agent. In a particular example, the device 800 includes a reservoir 804 that includes an osteogenerative agent and includes a reservoir 806 that includes a degradation agent. The reservoirs (804 or 806) can be configured to store the agent in a liquid, gel, paste, slurry, or solid form, or any combination thereof. A solid form can include powder, granule, microsphere, miniature rod, agent embedded in a matrix or binder material, or any combination thereof. In a solid form example, fluids or water from surrounding tissues can be absorbed by the device 800 and placed in contact with an agent in solid form prior to release. In a further example, the reservoir (804 or 806) can include a refill port.

A reservoir driver 812 can be coupled to the reservoir (804 or 806). As illustrated, the reservoir driver 812 can be coupled to both the reservoir 804 and the reservoir 806. Alternatively, a separate reservoir driver can be connected to each reservoir (804 or 806). An exemplary reservoir driver 812 can include a pump. For example, a pump can add fluid or water from surrounding tissue to a chamber that applies pressure to the reservoir (804 or 806), motivating an agent from the reservoir (804 or 806). In another example, the pump can add water or fluid directly to the reservoir (804 or 806) to increase pressure within the chamber or to hydrate a solid form agent within the reservoir (804 or 806).

In another example, the reservoir driver 812 can include an osmotic driver. For example, a membrane can separate a chamber from surrounding tissue. An osmotic agent within the chamber can absorb water or fluid from the surrounding tissue and expand or increase pressure within the chamber. The osmotic agent can include a non-volatile water-soluble osmagent, an osmopolymer that swells on contact with water, or a mixture of the two. An osmotic agent, such as sodium chloride with appropriate lubricants, binders, or viscosity modifying agents, such as sodium carboxymethylcellulose or sodium polyacrylate can be prepared in various forms. Sodium chloride in tablet form is a water swellable agent. The osmotic agent can generate between about 0 and about 36 MPa (about 5200 psi) of pressure. Materials suitable for the fluid permeable membrane include those that are semipermeable and that can conform to the shape of the housing upon wetting and make a watertight seal with the rigid surface of the housing. The polymeric materials from which the membrane can be made vary based on the pumping rates and device configuration requirements and can include plasticized cellulosic materials, enhanced polymethylmethacrylate such as hydroxyethylmethacrylate (HEMA), elastomeric materials such as polyurethanes and polyamides, polyetherpolyamide copolymers, thermoplastic copolyesters, or the like, or any combination thereof. The chamber can apply pressure to a movable barrier between the chamber and the reservoir (804 or 806), motivating agent from the reservoir (804 or 806).

In a further example, the reservoir driver 812 can include a mechanical system that motivates agent from the reservoir (804 or 806). For example, the mechanical system can include a piston, a rotating screw, or any combination thereof.

In the exemplary device 800, a control element, such as the control elements 808 or 810, can be connected to the reservoir, such as the reservoirs 804 or 806, respectively. The control element (808 or 810) can permit access to the respective reservoir (804 or 806). For example, the control element (808 or 810) can include a valve that permits fluid agent to exit the reservoir (804 or 806). In another example, the control element (808 or 810) can include a pump that removes fluid agent from the reservoir (804 or 806). In a further example, the control element (808 or 810) can include a door or rotating element that permits solid form agent to be pushed from the reservoir (804 or 806).

In an exemplary embodiment, the control element (808 or 810) and the reservoir driver 812 can be the same device. For example, a pump can both motivate the agent from the reservoir (804 or 806) and control the flow of the agent. In another example, a mechanical driver can act to both motivate and control the amount of agent exiting the reservoir (804 or 806).

In a further exemplary embodiment, the control element (808 or 810) can include a destructible or removable barrier. For example, individual reservoirs (804 or 806) can include a single dose of an agent. An array of reservoirs can be provided that each includes a removable barrier. Destruction or removal of the barrier exposes the contents of the reservoir to surrounding tissue. For example, the barrier can be a thin film that bursts when an agent within the reservoir is heated or activated. In another example, the barrier can be a film that when heated or exposed to electric current disintegrates, exposing a reservoir.

The device 800 also can include a memory 816 in communication with the controller 802. The controller 802 can store sensor data at the memory 816. In another example, the controller 802 can store parameter values that are accessed to determine control actions. For example, the controller 802 can store threshold values, model parameters, delay parameters, dosage parameters, or any combination thereof at the memory 816. As illustrated, the controller 802 is directly coupled to the memory 816. Alternatively, the controller 802 can communicate with a memory controller that in turn controls the memory 816. An exemplary memory 816 can include random access memory (RAM).

In addition, the device 800 can include a clock 822. The clock 822 can provide a time signal to the controller 802. The controller 802, for example, can use the time signal to time stamp sensor data. In another example, the controller 802 can use the time signal in performing calculations based on the sensor signal. For example, the controller 802 can select or weight sensor signals based on time of day. In another example, the controller can determine a minimum or maximum value of the sensor signal for a 24-hour period. In a further example, the controller 802 can determine a rate of change or a trend based on the time signal and sensor data. Alternatively, the controller 802 can use the clock 822 to determine a release time based on a release schedule.

The device 800 can further include a power supply 818. For example, the power supply 818 can include a battery. In an exemplary embodiment, the battery is a rechargeable battery. The power supply 818 can include a wireless power regeneration circuitry, such as an induction coil, or can include a recharging port. For example, the induction coil can respond to an electromagnetic signal and generate power for storage in a battery. In the example illustrated, the power supply 818 is coupled to the controller 802.

In an exemplary embodiment, the device 800 can include a remote access component 820. The remote access component 820 can be in communication with the controller 802. In an example, the remote access component 820 can respond to a magnetic field. In another example, the remote access component 820 can respond to an electromagnetic signal, such as a radio frequency signal. In a further example, the remote access component 820 can respond to a light signal, such as an infrared signal. In an additional example, the remote access component 820 can respond to a wave signal, such as an ultrasonic signal.

In response to a signal from the remote access component 820, the controller 802 can activate or change mode. In an example, the controller 802 can initiate control of the control element (808 or 810) or reading of the sensor (813 or 814) in response to a signal from the remote access component 820. In another example, the controller 802 can cease control or reading of components in response to a signal from the remote access component 820. In a further example, the remote access component 820 can be accessed to manually override programming of the controller 802. In another exemplary embodiment, the controller 802 can communicate data via an antenna included within the remote access component 820. For example, sensor data stored in the memory 816 can be transmitted via the antenna.

In a further exemplary embodiment, the remote access component 820 can receive data for use by the controller 802. For example, the data can include control parameters, dosage parameters, timing parameters for data storage, time and date, programming instructions, or any combination thereof. An exemplary control parameter includes a threshold value, an algebraic constant, a model parameter, or any combination thereof.

In an alternative embodiment, the device 800 can include a remote access component 820 that directly manipulates the control element (808 or 810) or the reservoir driver 812. For example, the remote access component 820 can directly manipulate the control element 808, such as a valve. In another example, the remote access component 820 can directly manipulate the reservoir driver 812. In a particular example, the device 800 includes a reservoir 804 including an agent, a reservoir driver 812 coupled to the reservoir and configured to effect the release of the agent from the reservoir 804, and a remote access component 820. In this particular example, the device 800 can be configured to manipulate the reservoir driver 812 to effect the release of the agent in response to a first signal received via the remote access component 820. For example, the control element 808 can be a valve that opens or closes in response to pressure in the reservoir 804. The reservoir driver 812 can increase the pressure in the reservoir 804 to open or close the valve. In addition, the device 800 can be configured to manipulate the reservoir driver 812 or the control element 808 to prevent release of the agent in response to a second signal received via the remote access component 820.

In a further example, the device 800 can include a second reservoir 808 including a second agent. For example, the first agent can be a degradation agent and the second agent can be an osteogenerative agent. In a device including a single reservoir driver 808, the reservoir driver 812 can be coupled to the second reservoir 808. In another embodiment, the device 800 can include a second reservoir driver coupled to the second reservoir 808. The device 800 can be configured to manipulate the second reservoir driver to effect the release of the second agent. In a particular embodiment, the remote access component 820 can be configured to communicate using an IEEE 802.15 communication protocol.

In a particular example, a patient in which the device 800 is implanted can experience pain or a test of the patient, such as a computed tomography (CT) scan or a magnetic resonance imaging (MRI) scan, can indicate a problem with the intervertebral disc or zygapophyseal joint in which the device 800 is implanted. A healthcare provider can manipulate the performance of the device 800 by accessing the remote access component 820.

Figure 8:
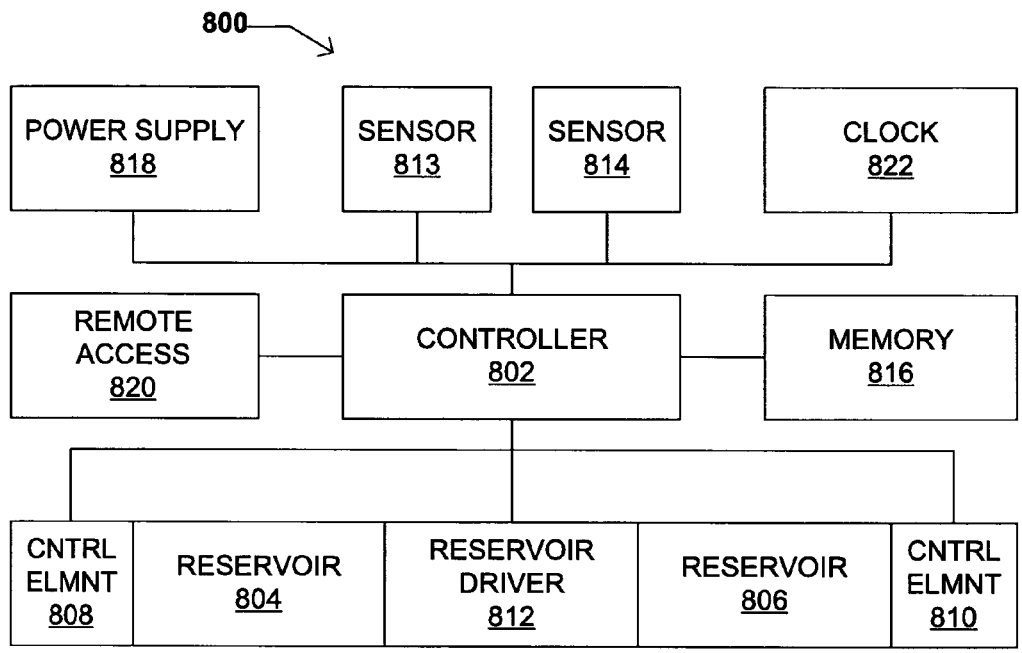
FIG. 8 includes a diagram of a controlled release device.

The device, such as device 800 illustrated in FIG. 8, can be included in a housing. The housing can form a cylinder, sphere, capsule, disc, cone, coil shape, or any combination thereof. In an example, the housing can surround each of the components of the device. Alternatively, the individual components can be included within one or more housings. For example, the controller can be included in a housing. The reservoir can be at least partially included within the housing, can extend beyond the boundaries of the housing, or can be separate from the housing. In another example, the sensor can be included in a housing with the controller, and the power supply and the remote access component can be housed separately.

The device 800 can include a housing configured based on the soft tissue in which the device is to be implanted. In particular, the smallest dimension of the housing can be configured to fit between osteal structures in proximity to the soft tissue. For example, when the soft tissue includes an intervertebral disc, the dimensions of the housing can be configured to fit between the superior and the inferior vertebrae. In another example, when the soft tissue includes a zygapophyseal joint, the housing can be configured to fit between articular processes of adjacent vertebrae. In an example, the housing can have a smallest dimension not greater than about 8 mm. For example, the smallest dimension can be not greater than about 5 mm, such as not greater than about 3 mm. In a particular example, a cylindrical housing can have a diameter that is not greater than about 8 mm. In an exemplary capsule-shaped housing, the diameter around the center is not greater than about 8 mm.

The housing can be formed of a metallic material, a polymeric material, or any combination thereof. An exemplary polymeric material can include polypropylene, polyethylene, halogenated polyolefin, fluoropolyolefin, polybutadiene, polysulfone, polyaryletherketone, polyurethane or copolymers thereof, silicone, polyimide, polyamide, polyetherimide, a hydrogel, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary hydrogel can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

Figure 9:
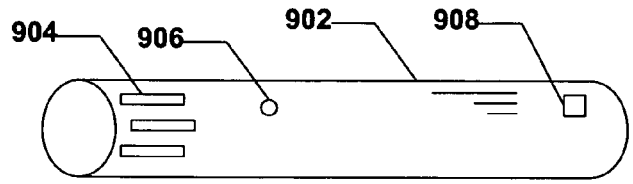
FIG. 9, FIG. 10, FIG. 11, FIG. 12, FIG. 13 and FIG. 14 include views of exemplary controlled release devices.

FIG. 9, FIG. 10, FIG. 11, FIG. 12, and FIG. 13 include illustrations of devices surrounded by housings. FIG. 9 includes an example of an exemplary device 902 that includes external ports 904 connected to control elements for providing access to reservoirs. In addition, the exemplary device 902 includes a port 908 coupled to a sensor via which the sensor can acquire data associated with the condition of surrounding tissue, such as the nucleus pulposus of an intervertebral disc or such as tissues of a zygapophyseal joint. In a further example, the device 902 can include a refill port 906 for refilling a reservoir with an agent.

Figure 10:
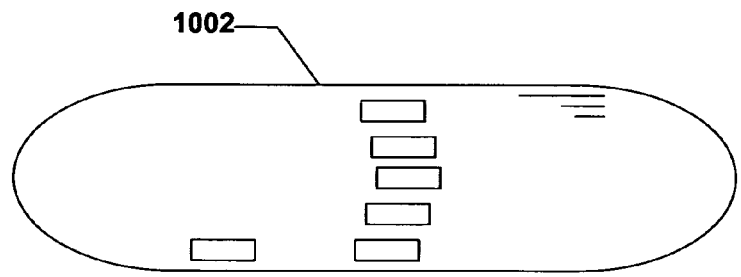
Figure 11:
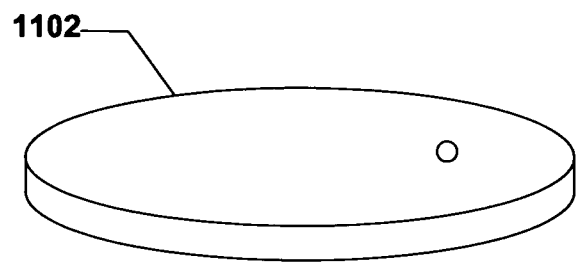

FIG. 10 illustrates another exemplary device 1002 in the shape of a capsule and FIG. 11 illustrates a further exemplary device 1102 in the shape of a disc. The exemplary devices 1002 and 1102 can include ports for sensor access, reservoir access, and refill access.

Figure 12:
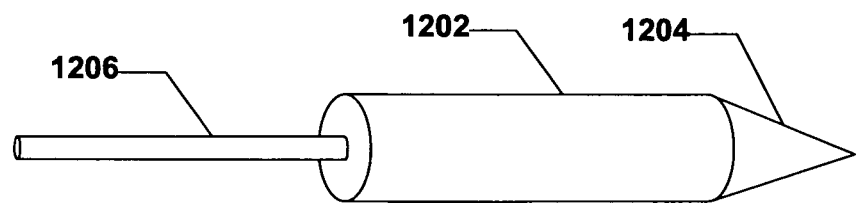

FIG. 12 includes a further exemplary device 1202. The device 1202 can include a conical end 1204 to assist with insertion of the device into an intervertebral disc or a zygapophyseal joint. The device 1202 can also include ports for refill, reservoir access, and sensor access. In addition, a reservoir 1206 can extend beyond the end of the housing. In a particular example, the reservoir 1206 can be flexible. As such, the reservoir 1206 can coil when inserted into a nucleus pulposus of an intervertebral disc or in proximity to a zygapophyseal joint.

Figure 13:
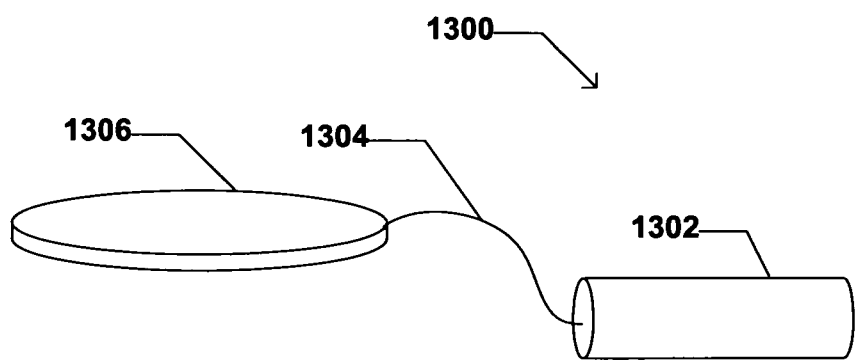

In another exemplary embodiment illustrated in FIG. 13, a device 1300 includes separate housings 1302 and 1306 connected by a transmission line 1304. In an exemplary embodiment, the housing 1302 can include a controller, a sensor, and a control element, and the housing 1306 can include a power supply and a remote access component. In such an example, power is transmitted along line 1304 to the controller in the housing 1302. In a further example, the housing 1302 can include a sensor and a control element and the housing 1306 can include a controller, a memory, and a remote access component. In such an example, sensor signals and control signals can be transmitted along transmission line 1304. In a particular example, the transmission line 1304 can include a conduit for an agent and an electrical signal line.

Figure 14:
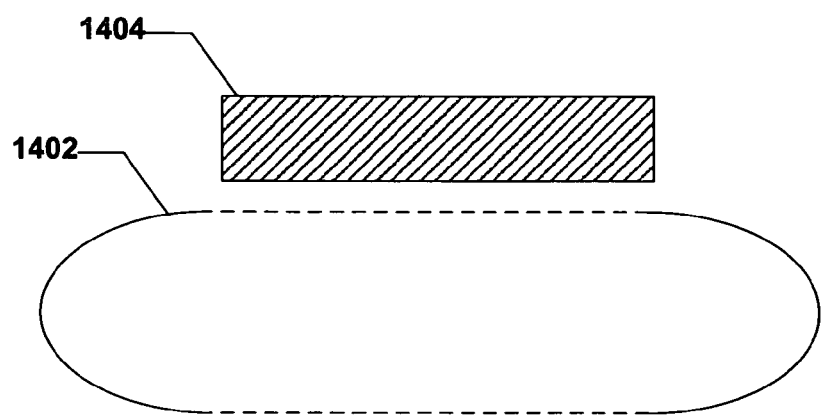

In a further exemplary embodiment illustrated in FIG. 14, an implantable device 1402 can include a structure 1404 configured to expand or extend. Such a structure 1404 can include a surface of the implantable device 1402 or can include a particular element of the device 1402. In particular, the structure 1404 can extend to engage an adjacent osteal structure, such as a process or vertebral body.

The device 1402 can include a mechanism to extend or expand the structure 1404. For example, the device can include a flexible container configured to expand when fluid, such as a gas or liquid is introduced. In particular, a fluid can be introduced into the device 1402 during implantation to extend the structure 1404 to a desired extension. In another example, the mechanism can be an osmotic device configured to expand in response to absorbed liquid from surrounding tissue, extending the structure 1404 to a configured extension. In a further example, the mechanism can include a screw device, an electrically driven device, or a wedge device. In particular, a wedge or solid component can be inserted into the device during the implanting process to extend the structure 1404.

For example, the structure 1404 can be extended to engage one or more osteal structures, such as vertebral bodies or processes. In such a manner, the device can be secured in place. In addition, the structure 1404 can act to encourage bone growth and can be osteoconductive.

Figure 15:
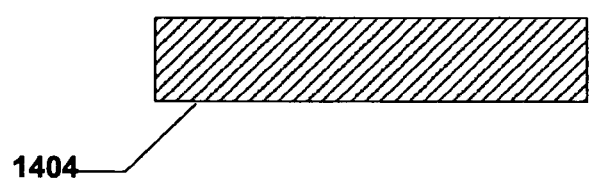
FIG. 15 and FIG. 16 include illustrations of exemplary surface topographies of a controlled release device.
Figure 16:
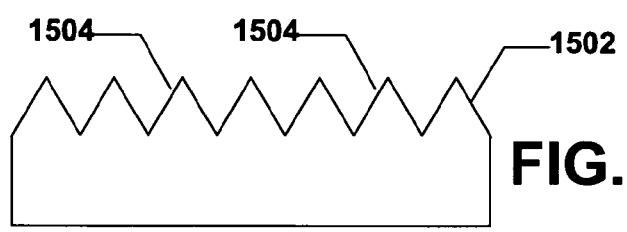

In a particular embodiment, the device 1402 can include a textured surface. Such a textured surface can be configured to secure the device to an osteal structure. In particular examples illustrated in FIG. 15 and in FIG. 16, an implantable device can have a surface, such as surface 1502 or surface 1602, with structures 1504 or serrations 1604, respectively. In an example, the structures 1504 or serrations 1604 can engage an osteal structure. In another example, the structures 1504 or serrations 1604 can irritate a soft tissue, such as a vertebral cartilaginous end plate, to further affect bone growth. Alternatively, a textured surface can be osteoconductive. For example, the structure 1404 can include osteogenerative material, including a bone graft, a bone graft substitute, a bone growth factor/carrier, an allograft, an autograft, or any combination thereof.

Figure 26:
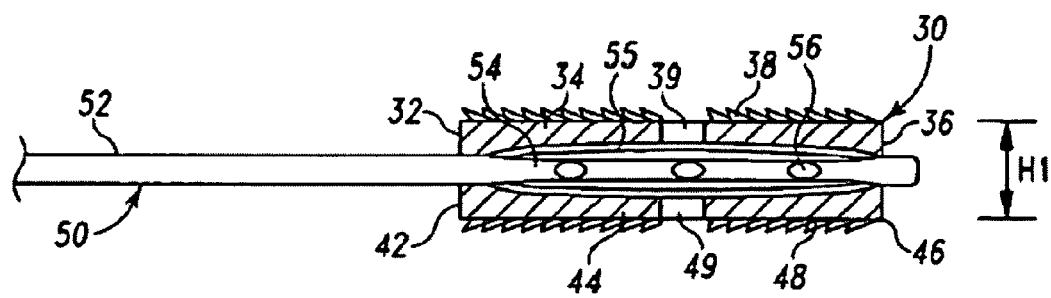
FIG. 26, FIG. 27, FIG. 28, FIG. 29, and FIG. 30 include illustrations of exemplary expandable components.
Figure 27:
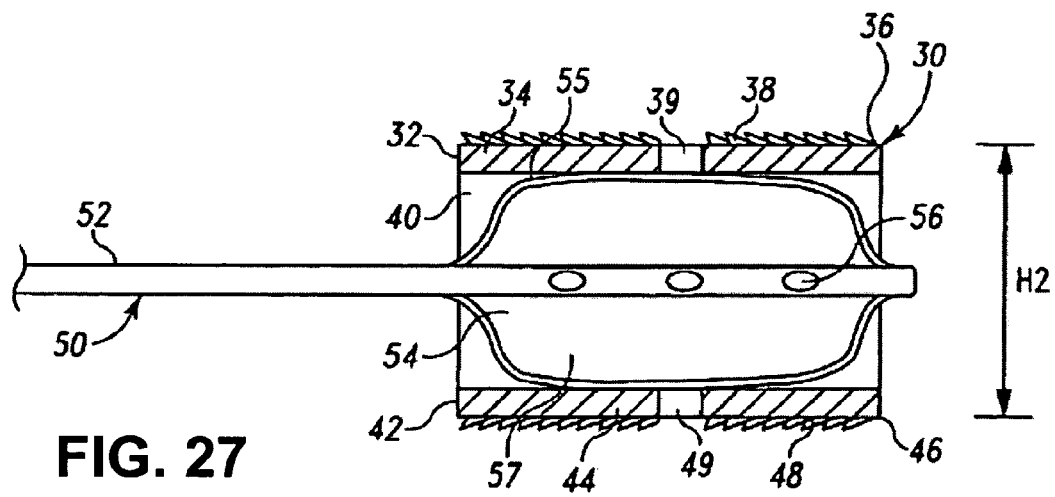

A further embodiment of an expandable mechanism 30 is illustrated in FIG. 26 and FIG. 27. In this embodiment, the expandable mechanism 30 can include an elongated body positionable in a spinal disc space that includes a first portion 34 positionable along one endplate of a first vertebra and a second portion 44 positionable along the endplate of an adjacent second vertebra. The first portion 34 can extend between a distal leading insertion end 36 and a proximal trailing end 32. The second portion 44 can extend between a distal leading insertion end 46 and a proximal trailing end 42. A cavity 40 can be defined between the first portion 34 and the second portion 44. The cavity 40 can extend between and open at the distal end 36 and the trailing end 32.

The first portion 34 can be provided with a number of protrusions 38, and the second portion 44 also can be provided with a number of protrusions 48. The protrusions 38, 48 can be configured to engage bony tissue of the vertebrae, and can be in the form of teeth, spikes, ridges, threads, barbs, knurlings, fins, and combinations thereof, for example. Alternatively, the outer surfaces can be smooth, or auxiliary fixation or engagement members can be provided. The first and second portions 34, 44 can further include one or more openings 39, 49, respectively, to facilitate bone growth.

The first portion 34 and the second portion 44 are movable away from one another from an unexpanded configuration, as illustrated in FIG. 26, to an expanded configuration, as illustrated in FIG. 27. In the unexpanded configuration, the expandable mechanism 30 has a height H1 between the first portion 34 and the second portion 44. In the expanded configuration, the expandable mechanism 30 has a height H2 between the first portion 34 and the second portion 44. The height H1 can allow the expandable mechanism 30 to be inserted, for example, in a disc space between adjacent vertebral bodies. The height H2 can correspond to a separation height between the first and the second portions 34, 44 to provide a desired disc space height between adjacent vertebrae.

A delivery instrument 50 can be provided to move the expandable mechanism 30 from its unexpanded configuration to its expanded configuration. The delivery instrument 50 can include a proximal shaft 52 and a distal portion 54 including an expandable element 55. In the illustrated embodiment, expandable element 55 is an inflatable balloon-like structure having a collapsed configuration, as illustrated in FIG. 26, and an enlarged, inflated configuration, as illustrated in FIG. 27. The shaft 52 can be provided with a lumen through which fluid or material can be supplied through openings 56 to an internal volume 57 of the expandable element 55 to enlarge or inflate the expandable element 55. The expandable element 55 can be positionable in the cavity 40 of the expandable mechanism 30 with each of the expandable element 55 and the expandable mechanism 30 in its unexpanded or collapsed configuration.

After delivery of the expandable mechanism 30 to the operative site, the expandable element 55 can be inflated to provide an enlarged configuration for the expandable element 55 and thus, separate the first and second portions 34, 44 of the expandable mechanism 30. As the expandable mechanism 30 is expanded, the first portion 34 and the second portion 44 move away from one another and the volume of the cavity 40 is increased. The expansion can distract adjacent vertebra to provide a desired spacing between the adjacent endplates and to restore a disc space height.

An example of a suitable delivery instrument 50 includes a high-pressure balloon catheter. The shaft 52 can be rigid, semi-rigid, or flexible. The shaft 52 can be fabricated from metals, polymers, or combinations thereof. The shaft 52 can be provided with at least one lumen to allow inflation or enlargement of the expandable element 55 with a biocompatible fluid, such as air or saline, for example. In another example, the shaft 52 includes multiple lumens to, for example, deliver bone graft, bone growth material or other suitable filler material into the expanded cavity 40 of an expanded mechanism 30. The expandable element 55 can be collapsed prior to or simultaneously with placement of the filler material.

In the illustrated embodiment, the distal portion 54 includes a single expandable element 55, although multiple expandable elements are also contemplated to provide the distal portion 54 with alternate enlargement characteristics. For example, the distal portion 54 can include a distal expandable element and a proximal expandable element having differing heights to provide angulation between the expanded first and second portions 34, 44 of the expandable mechanism 30. In another example, the distal portion 54 can include an upper expandable element and a lower expandable element which can be selectively expanded to move the adjacent one of the first and second portions 34, 44 while the other of the first and second portions remains stationary. In a further example, the expandable element 55 can expand uni-directionally to move the adjacent one of the first and second portions 34, 44 in the direction of expansion.

In another embodiment, the distal portion 54 can be severed from the shaft 52 after expansion, and post-operatively maintain the expandable mechanism 30 in an expanded condition. Accordingly, the expandable element 55 can be inflated with bone growth material or other suitable filler material to facilitate bone growth or preserve motion of the intervertebral space through the expanded mechanism 30. When the filler material suitably hardens in the expandable element 55 to prevent flow from extending therefrom, the shaft 52 can be removed. Alternatively or additionally, a valve arrangement can be provided adjacent expandable element 55 to prevent the filler material from exiting therefrom. The expandable element 55 can be fabricated from porous material, resorbable material, or other suitable material to allow bone growth through the cavity of the expanded device. In a further embodiment, the expandable element 55 is inflated with a polymer that is flowable into the expandable element and thereafter polymerizes to form an elastic core between the first and second portions 34, 44.

The expandable element 55 can include a size and shape that matches the size and shape of the cavity 40 in its expanded configuration, although non-matching configurations are also contemplated. In the expanded configuration, the expandable element 55 can apply a uniform expansion force along the inner wall surfaces of first portion 34 between leading end 36 and trailing end 32. If configured for bi-directional expansion, the expandable element 55 can apply a uniform expansion force along the second portion 44 between leading end 46 and trailing end 42. The uniform expansion force distributes the distraction loads along the adjacent vertebral endplate to provide uniform distraction along the length of expandable mechanism 30. The expandable element 55 or the cavity 40 can be provided with any suitable overall shape including conical, frusto-conical, spherical, cubic, spherical, polygonal, ovoid, long conical, long spherical, rectangular, tapered, stepped, dog-bone shape, offset shapes and combinations thereof.

The expandable element 55 can be made from any suitable material capable of withstanding the pressure supplied to enlarge or inflate expandable element 55 in situ. An exemplary material includes a polymeric material, such as polyethylene terephthalate, polyolefin, polyurethane, nylon, polyvinyl chloride, silicone, or any combination thereof.

Figure 28:
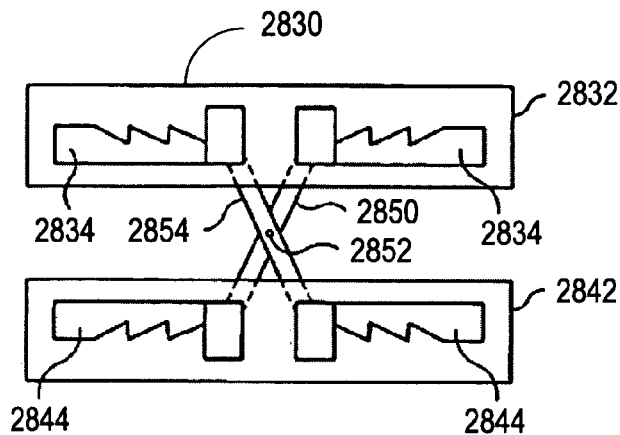

In another exemplary embodiment illustrated in FIG. 28, the expandable mechanism 2830 can include a first portion 2832 and a second portion 2842. Linkages 2850 can movably couple the first and second portions 2832, 2842 to one another and can include first and second members 2852, 2854 pivotally coupled to one another. The members 2852, 2854 each can include a first end positioned in respective ones of receptacles 2834 of first portion 2832, and opposite second ends positioned in respective receptacles 2844 of second portion 2842. The ends of the members 2850, 2852 can include a configuration that interdigitates with a ratchet surface formed along the respective receptacles 2834, 2844.

In the unexpanded configuration, the ends of members 2852, 2854 are positioned at the outer ends of the respective receptacles 2834, 2844. As the first and second portions 2832, 2842 are bi-directionally moved away from one another, the ends of members 2850, 2852 can move longitudinally toward one another along the receptacles 2834, 2844 of each of the respective first and second portions 2832, 2842, as illustrated in FIG. 28. The rigid members 2852, 2854 can move the first and second portions 2832, 2842 away from one another, and engage the ratchet surfaces along receptacles 2834, 2844 to maintain the expanded or separated position between the first and second portions 2832, 2842. Accordingly, the expandable device 2830 is vertically collapsible to facilitate insertion in a collapsed disc space with the delivery instrument, and thereafter vertically expandable to distract the disc space and maintain distraction post-operatively.

Figure 29:
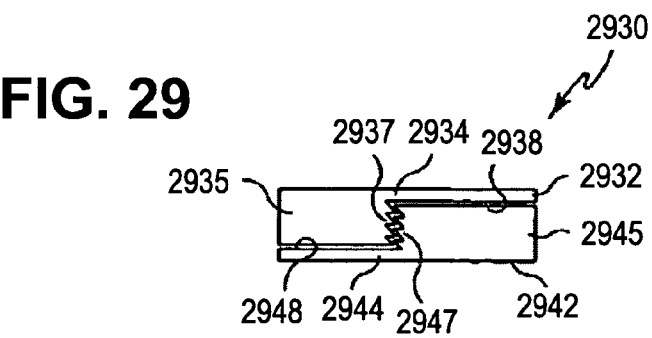

In another example of an expandable mechanism illustrated in FIG. 29, expandable mechanism 2930 includes a first portion 2932 and a second portion 2942. The first portion 2932 includes sidewalls 2934 that each can include an arm 2935. A receptacle 2938 is formed along one end of the arm 2935. The arm 2935 includes engagement surfaces 2937 extending along receptacle 2938. A second portion 2942 similarly includes sidewalls 2944 that each can include an arm 2945 and a receptacle 2948. The arm 2945 can be received in receptacle 2938, and the arm 2935 can be received in receptacle 2948. The arm 2945 can include engagement surfaces 2947 extending therealong that are engageable with the adjacent engaging surfaces 2937 of the arm 2935 of first portion 2932. The engagement surfaces 2937, 2947 can interdigitate and engage one another to maintain the expandable mechanism 2930 in an expanded condition.

Figure 30:
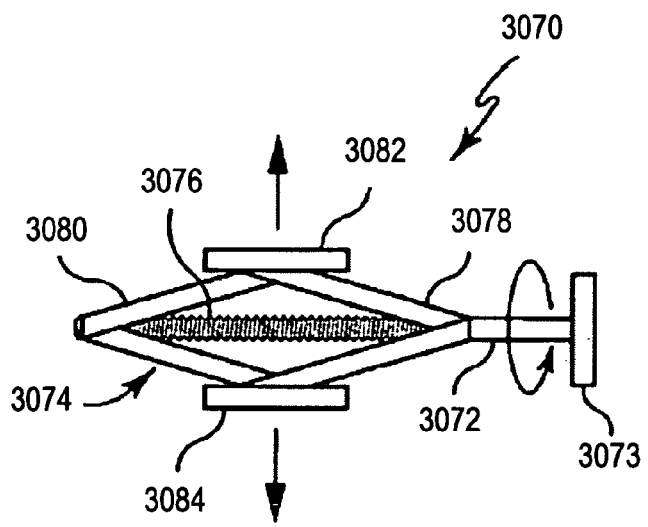

In a further example illustrated in FIG. 30, an expandable mechanism 3070 can include a shaft 3072 that can include a proximal handle portion 3073 and a distal portion 3076 extending through the expandable element 3074. The expandable element 3074 can include a first pivoting linkage 3078 and a second pivoting linkage 3080. The linkages 3078, 3080 each can include an intermediate pivot point engaged to and movable with the distal portion 3076. The linkages 3078, 3080 further can include distraction members 3082, 3084 coupled at the upper and lower ends thereof. The distal portion 3076 can be coupled to linkages 3078, 3080 so that, as the shaft 3072 is rotated about its axis with handle portion 3073 as indicated in FIG. 30, the pivoting intermediate portions of the linkages 3078, 3080 are drawn toward one another to move the distraction members 3082, 3084 away from one another.

Figure 31:
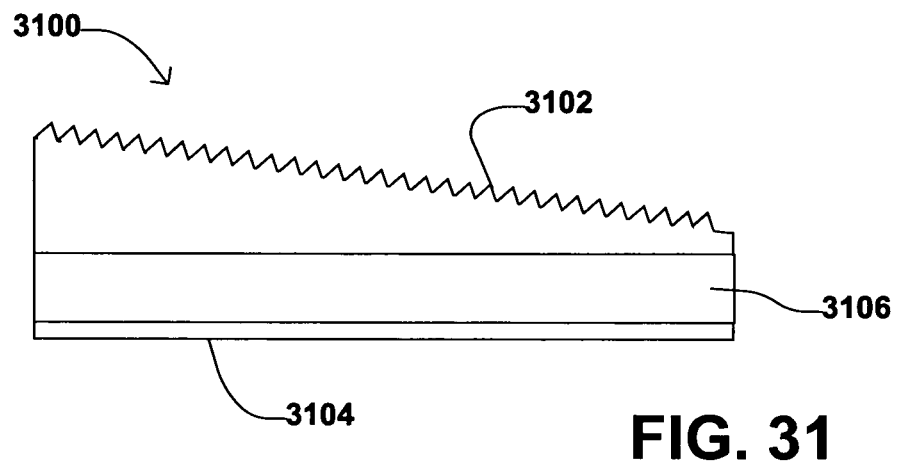
FIG. 31 and FIG. 32 include illustrations of exemplary spacer devices.
Figure 32:
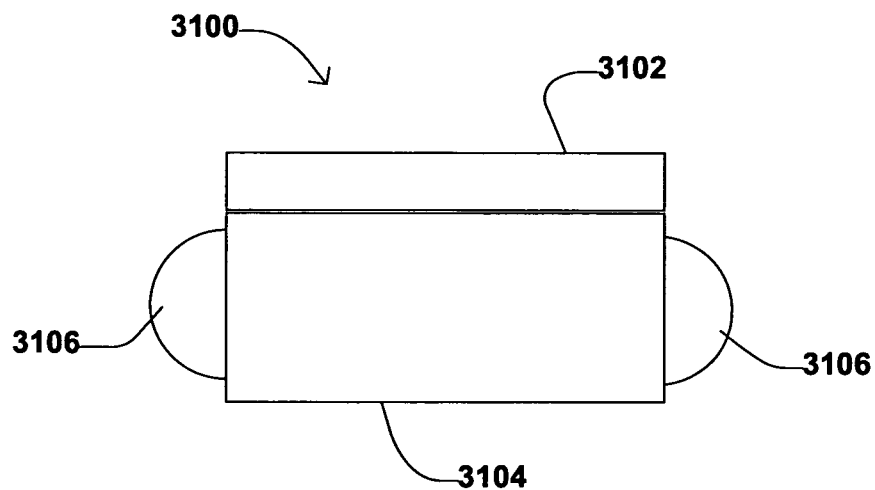

In another example illustrated in FIG. 31 and FIG. 32, the device 3100 can form a spacer. For example, the device 3100 can include surfaces 3102 and 3104 to engage a superior and an inferior vertebrae. In an example, the surface 3102 can include serrations or texture to engage the vertebrae. In another example, the surface 3104 can be smooth. Alternatively, the surfaces 3102 and 3104 can be smooth, textured, or serrated. In addition, the device 3100 can include reservoirs 3106 that extend along an edge of the device 3100. While the device 3100 is illustrated as a wedge, the device 3100 can be configured to have a rectangular, other polygonal, or circular cross-section, or any combination thereof. In a particular example, the device 3100 can have a height of about 0.5 mm to about 4 mm for a zygapophyseal joint implant or can have a height of about 5 mm to about 17 mm for a intervertebral disc implant.

Alternatively, the implantable device can be used in conjunction with other immobilizing devices. For example, the implantable device can be used in conjunction with a screw, a rod and screw system, a separate spacer, a separate fusion cage, interior plate, interspinous spacer, or any combination thereof. In particular, an implantable device can be inserted into an intervertebral disc or one or both of the zygapophyseal joints and the zygapophyseal joints can further be secured with screws. In another example, implantable devices can be used in conjunction with a rod and screw system, such as a percutaneous rod system, for example, a SEXTANT® system, available from Medtronic Sofamor Danek. In a further example, the implantable device can be implanted with a resorbable spacer.

Figure 17:
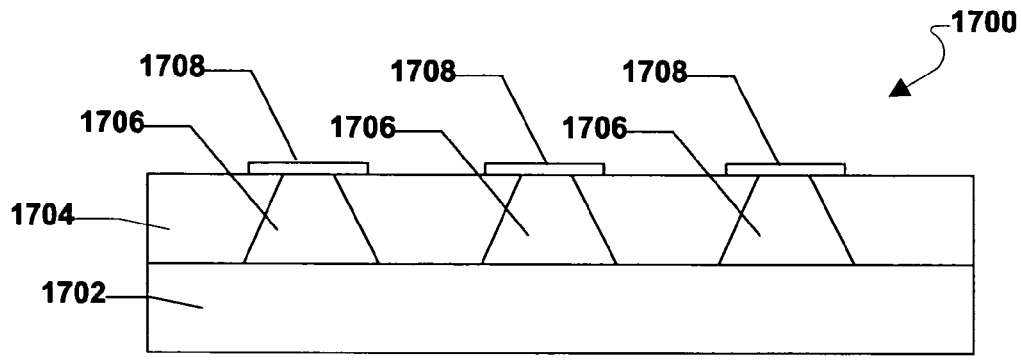
FIG. 17 includes a cross section view of an exemplary reservoir portion of an exemplary controlled release device.

In an alternative embodiment, the implanted device can include an array of reservoirs. For example, FIG. 17 includes an illustration of an exemplary array 1700 of reservoirs. For example, a device can include a substrate 1702. Imposed over the substrate can be a layer 1704 forming an array of reservoirs 1706. The array of reservoirs 1706 can each include an agent. Alternatively, a first subset of the array of reservoirs 1706 can include a first agent and a second subset of the array of reservoirs 1706 can include a second agent. Each reservoir 1706 is separated from surrounding tissue by a removable or destructible barrier 1708. In an exemplary embodiment, the barrier 1708 can burst in response to expansion of a substance included in the reservoir 1706. For example, the substance can expand in response to heat or electrical current. In a further example, heat or an electrical current can be applied to the barrier 1708, causing the barrier to disintegrate, exposing the agent in the reservoir 1706 to surrounding tissue. Exemplary barrier materials include metals such as copper, gold, silver, and zinc, and some polymers. An exemplary polymer has a melting point above body temperature. When the local temperature near the polymer barrier layer is increased above the polymer's melting point by, e.g., thin film resistors located near the barrier layer, the barrier layer melts and exposes the contents of the reservoir to the surrounding environment.

Exemplary Methods of Use

Figure 18:
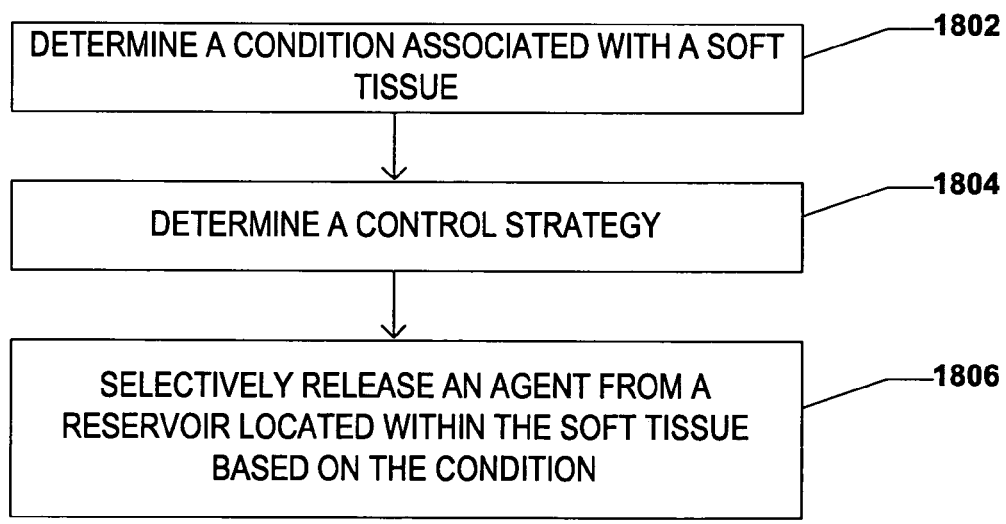
FIG. 18, FIG. 19, and FIG. 20 include block flow diagrams of exemplary methods for use by an exemplary controlled release device.

In an exemplary method, a device can be inserted into or proximate a soft tissue adjacent an osteal structure. The device can include a controller that measures a condition associated with the soft tissue, such as a surrounding nucleus pulposus or a zygapophyseal joint, and releases an agent based on the measurement. As illustrated at 1802 of FIG. 18, the device can determine a condition associated with the soft tissue. For example, the device can include a sensor, such as a pressure sensor, moisture sensor, resistivity or conductivity sensor, pH sensor, or any combination thereof. The device can use signals from the one or more sensors to determine a condition of the soft tissue. For example, a high average pressure measurement or a pressure measurement that is high at a particular time of day can indicate hydrated tissue in proximity to the implanted device. In contrast, a low average pressure measurement can indicate a low hydration or a low amount of soft tissue structures in proximity to the implantable device. In another example, a moisture sensor can indicate a high or low hydration level. In a further example, a combination of pressure data and moisture data can be used in determining the condition of the soft tissue. In an additional example, a trend in data from one or more sensors or a rate of change of a sensor measurements can be used to determine a condition of the soft tissue.

Based on the condition of the nucleus pulposus, the controller can determine a control strategy, as illustrated at 1804. For example, the controller can select an agent to be dispensed and can determine a dosage to be dispensed. In the particular examples illustrated in FIG. 6 and FIG. 7, the controller can release agents in accordance with the control strategy 600 or 700. In the strategy 600 illustrated in FIG. 6, for a moderate pressure or hydration level, no agent is released, and for a high pressure or hydration level, a degradation agent can be released, as illustrated at 602. For low pressure or hydration levels, an osteogenerative agent can be released, as illustrated at 604. In the strategy 700 illustrated in FIG. 7, the release profiles 702 and 704 for the degradation agent and the osteogenerative agent can overlap.

In response to determining the condition of the nucleus pulposus, the controller can initiate the release of an agent. For example, the controller can selectively release an agent from a reservoir based on the condition, as illustrated at 1806. The reservoir can be at least partially located within the soft tissue. In a particular example, the controller can select an agent to release, determine a dosage or amount of agent to release, and manipulate a control element, based on the determined condition of the soft tissue.

Figure 19:
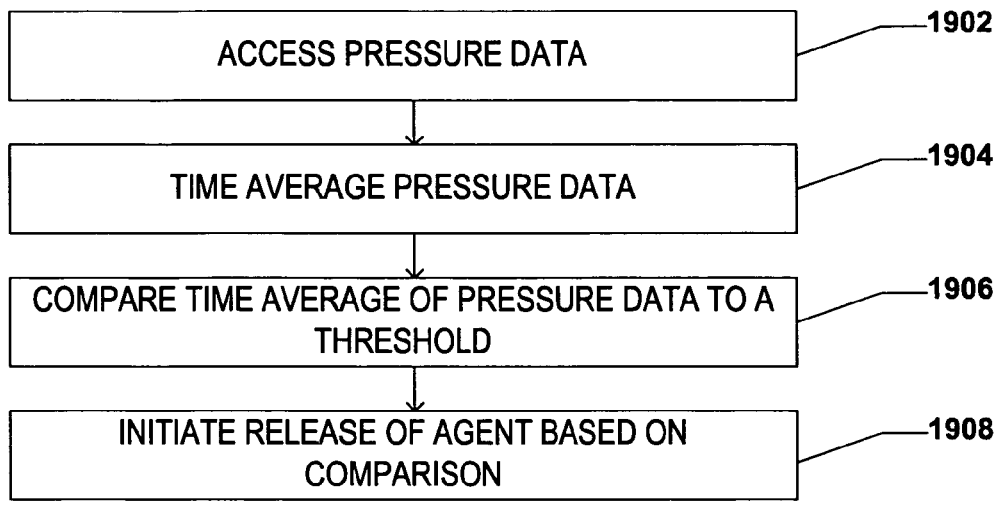

In a particular embodiment, the device can access pressure data, as illustrated at 1902 of FIG. 19. For example, the device can receive pressure data from a sensor or can retrieve pressure data from memory. The device can average the pressure data, such as determine a time average mean of the pressure data, as illustrated at 1904. In another example, the device can average a minimum pressure or a maximum pressure for a set of days. In a further example, the device can average pressure measured at a particular time of day, such as when a patient is inactive.

The device can compare the average of the pressure data to a threshold, as illustrated at 1906. For example, the threshold can be a low level threshold below which an osteogenerative agent is to be released. In another example, the threshold can be a high level threshold above which a degradation agent is to be released.

Based on the comparison to the threshold, the device can release an agent, as illustrated at 1908. For example, a controller can activate a control element associated with a reservoir including the agent to be released. In another example, the controller can activate a reservoir driver.

In another exemplary embodiment, a motion sensor, such as a relative motion sensor, or stress sensor can detect motion or stress in the tissue. In response, the device can release agent, such as osteogenerative agent. The device can subsequently delay release and await further detection of motion or stress.

Figure 20:
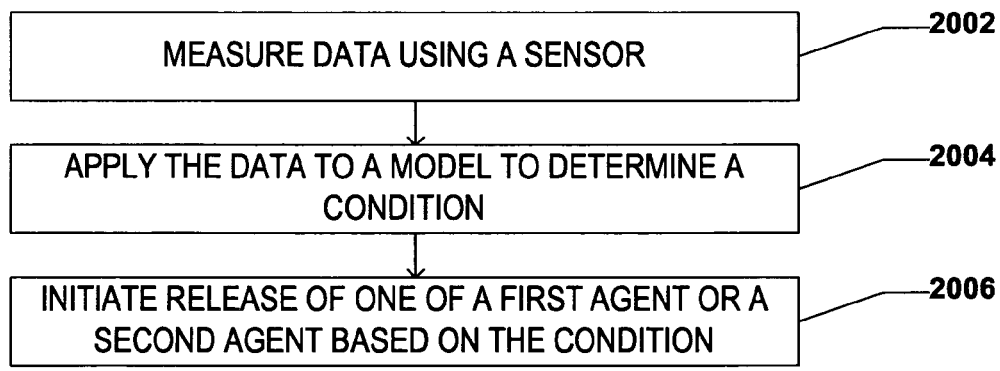

In another exemplary embodiment, a model can be used to determine when and how much agent is to be released. For example, data can be measured by one or more sensors, as illustrated at 2002 of FIG. 20. The data can be applied to a model to determine a condition of the soft tissue or determine dosages and agents to be release in association with the condition of the soft tissue, as illustrated at 2004. An exemplary model can include an algebraic model, a neural network model, a fuzzy logic model, or any combination thereof.

Based on the output of the model, the device can initiate release of a first agent or of a second agent, as illustrated at 2006. For example, when a soft tissue is dehydrated, an osteogenerative agent can be released. In another example, when pressure within the soft tissue is high, a degradation agent can be released.

Device Implantation

Figure 21:
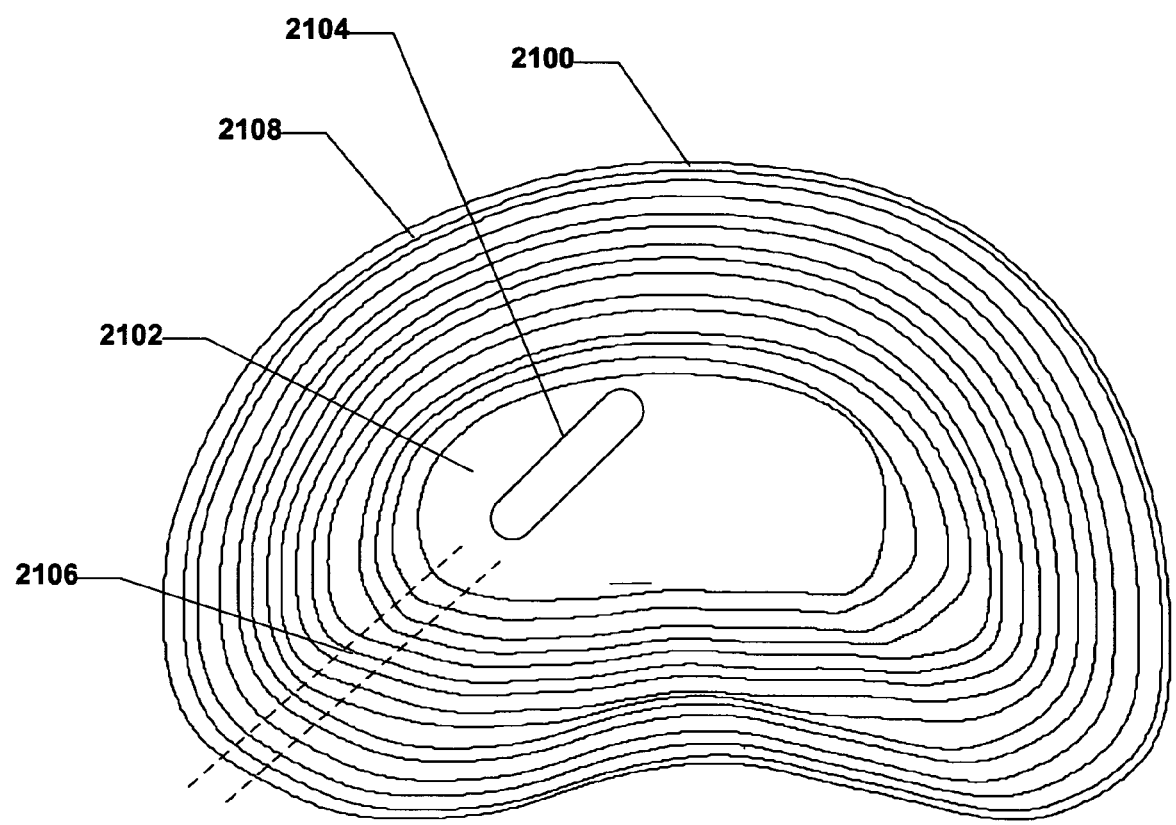
FIG. 21, FIG. 22, FIG. 23, and FIG. 24 include illustrations of exemplary controlled release devices in vivo.

The device or at least a portion of the device can be inserted into the nucleus pulposus of an intervertebral disc of a patient or into a zygapophyseal joint of a patient. For example, the device can be implanted as a whole within the nucleus pulposus or within the zygapophyseal joint. In another example, the device can be place in proximity to the zygapophyseal joint. FIG. 21 includes an illustration of a device 2104 implanted within the nucleus pulposus 2102 of an intervertebral disc 2100. The device 2104 can be inserted through a passage 2106 in the annulus fibrosis 2108 of the intervertebral disc 2100. In an example, the passage 2106 is formed and a cannula or an instrument having a lumen therethrough can be used to guide the device 2104 through the passage 2106. Once the device 2104 is inserted into the nucleus pulposus 2102, the passage 2106 in the annulus fibrosis 2108 can be sealed using a tissue sealant, scaffold plug, or any combination thereof. In a particular example, the tissue sealant or scaffold plug includes regenerative agents, such as growth factors. A similar method can be used to insert the implantable device into a zygapophyseal joint.

Figure 22:
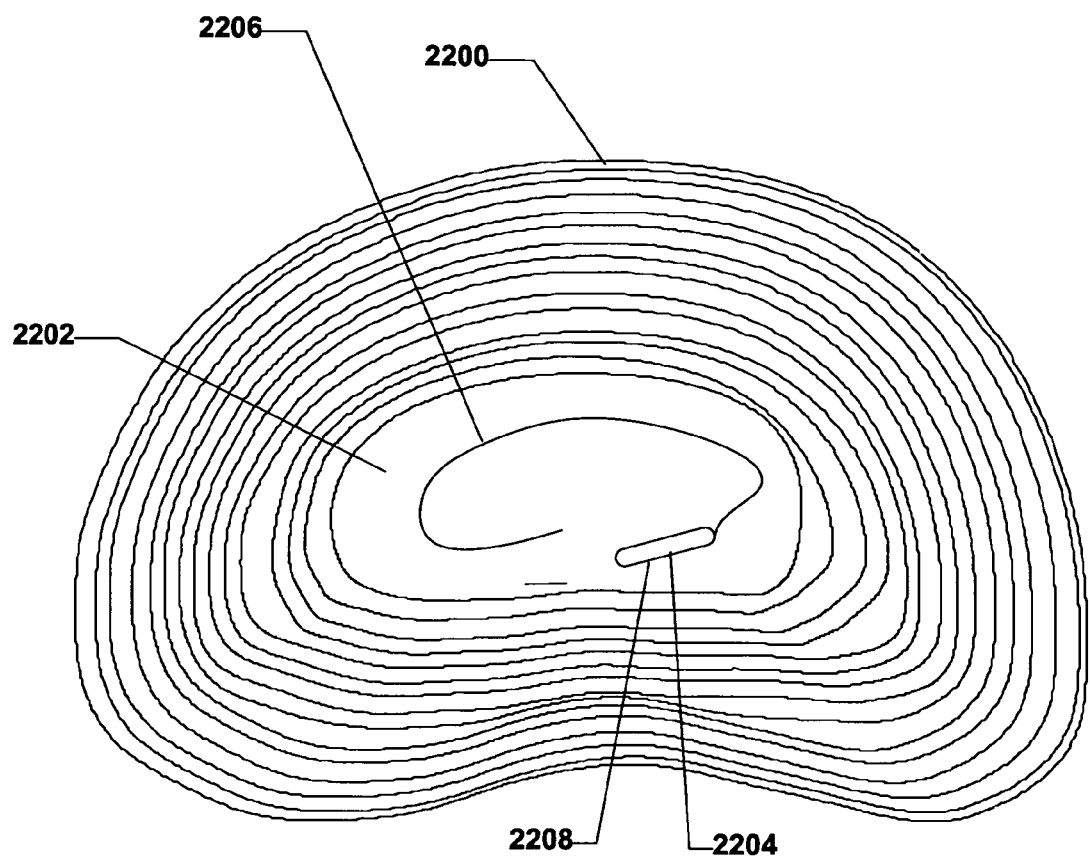

In another exemplary embodiment illustrated in FIG. 22, a device 2204 includes a head 2208 and a flexible tail 2206. The device 2204 can be inserted wholly within the nucleus pulposus 2202 of an intervertebral disc 2200 using the method described above in relation to FIG. 21. The head 2208 can include, for example, a sensor and a controller. The tail 2206 can include a portion of a reservoir. In another example, the tail 2206 can include an antenna. Alternatively, the device 2204 can be placed in or around a zygapophyseal joint.

Figure 23:
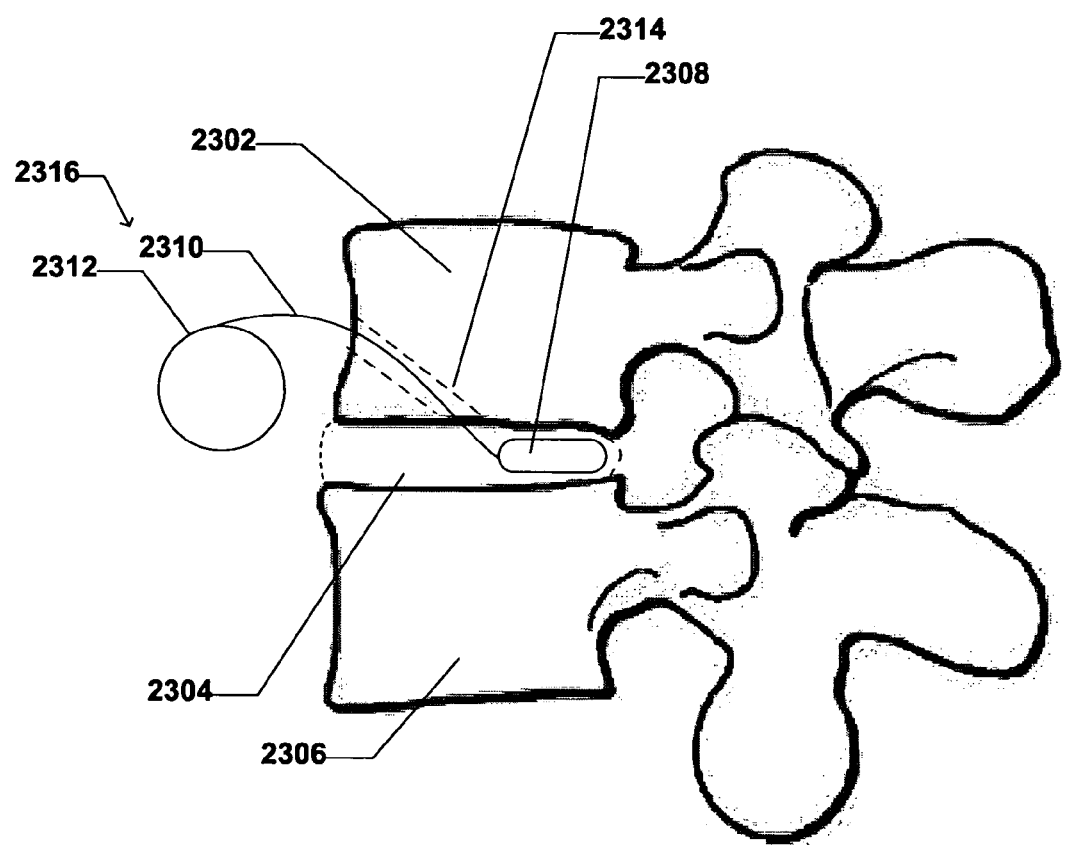

In an alternative embodiment illustrated in FIG. 23, the device can be inserted into the nucleus pulposus of an intervertebral disc 2304 through one of a superior vertebra 2302 or an inferior vertebra 2306. As illustrated in FIG. 23, a portion of the device can be inserted through the vertebral body and the end plate of the superior vertebra 2302. For example, an access 2314 can be drilled through the vertebral body and the end plate of the superior vertebra 2302. A head 2308 of the device 2316 can be guided through the access 2314 into a nucleus pulposus of the intervertebral disc 2304. A transmission line 2310 can traverse the access 2314 and connect the head 2308 to a tail 2312 of the device 2316. The access 2314 can be sealed with a ceramic material, bone cement, tissue sealant, or any combination thereof.

In an exemplary embodiment, the head 2308 can include a sensor, a controller, and a control element, and the tail 2312 can include a power supply, a remote access component, and a reservoir refill port. The reservoir can be located at the head 2308 or partially in the tail 2312.

In an alternative example, the head 2308 can include a sensor and a control element. The tail 2312 can include a controller, a memory, a power supply, a remote access component, and at least a portion of a reservoir. As such, the controller can receive data from the sensor and activate the control element from the tail 2312. While two embodiments of the device 2316 are disclosed above, other embodiments can be envisaged.

Figure 24:
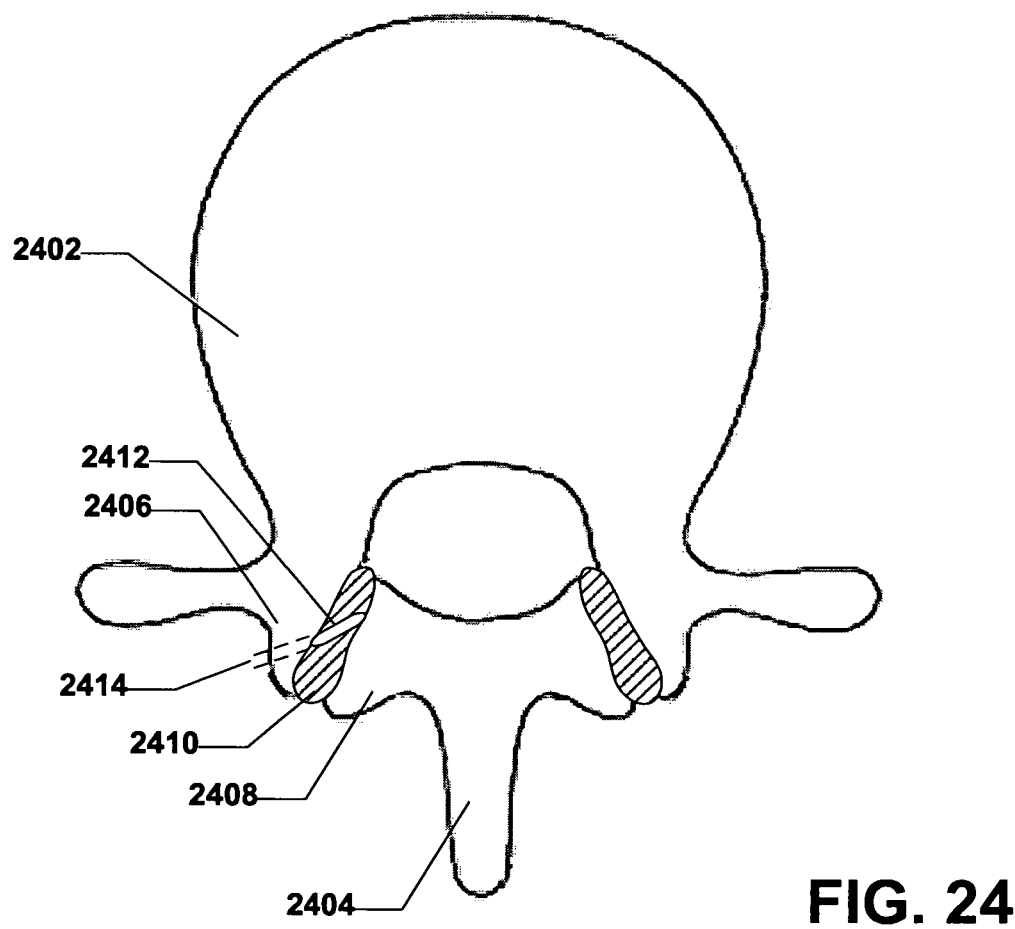

In a further exemplary embodiment illustrated in FIG. 24, an implantable device 2412 is inserted into a zygapophyseal joint 2410 through an articular process, such as a superior articular process 2406 of an inferior vertebra 2402. Alternatively, the implantable device 2412 can be inserted through the inferior articular process 2408 of the superior vertebra 2404. In an exemplary embodiment, the implantable device 2412 is inserted through an access 2414 drilled into an articular process. The device 2412 can engage one or both of the articular processes 2406 or 2408. Alternatively, the device 2412 can be positioned within the zygapophyseal joint to not engage the articular processes 2406 or 2408. While the device 2412 is illustrated without a tail and having a single housing, the device 2412 can be configured with a tail or with an additional housing. The access 2414 can be sealed with a ceramic material, bone cement, tissue sealant, or any combination thereof.

In a particular embodiment, implantable devices can be inserted into the intervertebral disc and the two articular processes associated with two adjacent vertebrae. As such, the implanted devices can influence bone growth to fuse the two adjacent vertebrae together at three locations: between the vertebral bodies, between the left articular processes, and between the right articular processes.

In an exemplary embodiment, a healthcare provider can monitor the device. Based on the data received from the device, the healthcare provider can adjust treatment of the patient, such as changing a setting of the device or injecting an additional agent. For example, once osteogeneration has been initiated, the healthcare provider can inject or implant additional osteogenerative material. For example, the healthcare provider can inject an osteoconductive gel or additional cellular material, such as stem cells. In another example, the healthcare provider can inject an osteoconductive material, such as collagen; a calcium phosphate, such as hydroxyapatite, tricalcium phosphate, or fluorapatite; demineralized bone matrix; calcium sulfate; or any combination thereof. In particular, a surgeon can inject stem cells that respond to the osteogenerative agent being release from the implanted device. In a particular embodiment, the stem cells can be injected into a refill port of the implantable device.

Patient Treatment Using an Implantable Device

Typically, the embodiments of the implantable controlled release device described above can be used to treat conditions associated with an intervertebral disc. For example, a patient can have undergone a prior discectomy or can have experienced a herniated disc. In another example, a scan of the patient, such as a computed tomography (CT) scan or a magnetic resonance imaging (MRI) scan, can indicate a problem in a particular intervertebral disc. In such a case, a device can be implanted in the patient.

In general, the device can be preprogrammed and filled with an agent prior to implantation. For example, the device can include an access port to transfer data, such as dosage data and control data into the device. In another example, the device can include a wireless access circuitry, such as a radiofrequency circuitry, an infrared circuitry, or an ultrasonic circuitry for receiving data. In an example, the wireless access circuitry can be proprietary or can conform to a wireless communication standard, such as IEEE 802.11, IEEE 802.15, or IEEE 802.16. In a particular example, the wireless access circuitry can be Bluetooth® compatible. Such data can be determined by a physician or healthcare practitioner prior to inserting the device. Software can be provided to configure the device for a particular patient.

The device can be included in a kit that includes agents to be inserted into the device. Alternatively, the device can be provided with the agent within the device. In addition, the device can include a refill port. An agent can be injected into the port to refill a reservoir.

Figure 25:
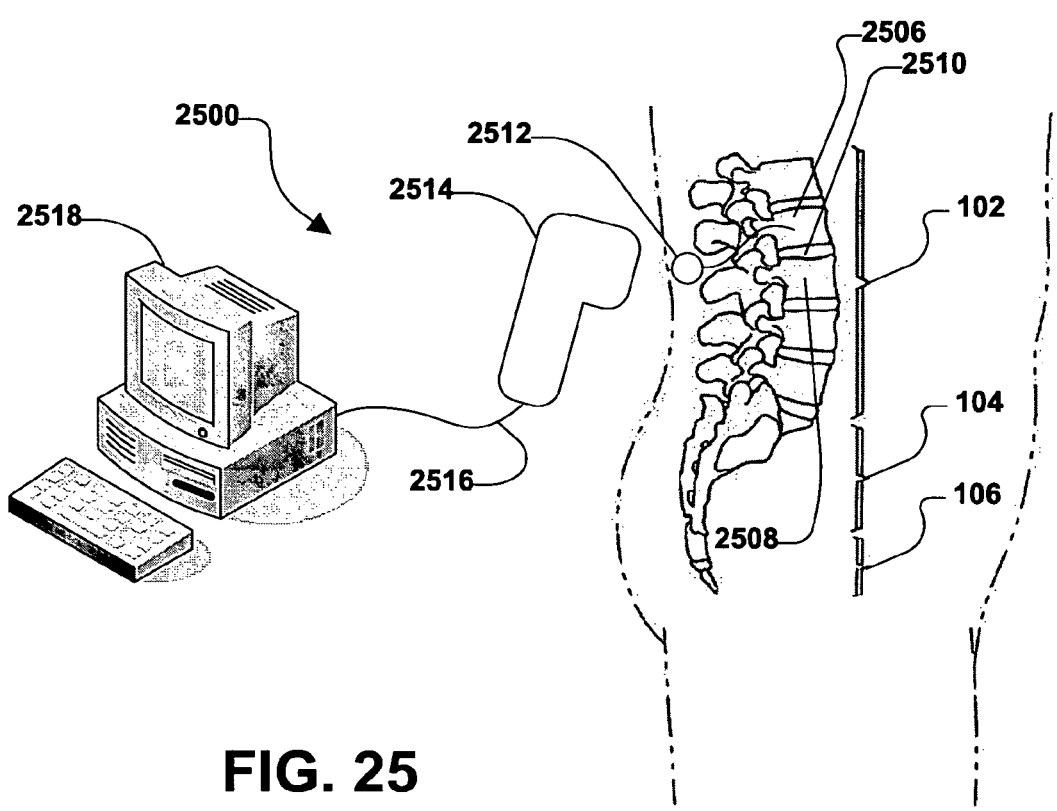
FIG. 25 includes an illustration of an exemplary controlled release system.

In a particular embodiment, the device can provide feedback to a physician or healthcare practitioner when implanted. In the example illustrated at FIG. 25, a device 2512 can be implanted in the spine 2504 of a patient 2502. For example, the device 2512 can include a portion that is inserted in an intervertebral disc 2510 between two vertebrae 2506 and 2508 or alternatively, a zygapophyseal joint.

The device 2512 can include a wireless access circuitry or a remote access component. A remote access device 2514 located external to the patient 2502 can communicate with the remote access component of the device 2512. For example, the remote access device 2514 can read data from the device 2512. In another example, the remote access device 2514 can transmit parameters or programming instructions to the device 2512.

In a particular embodiment, the remote access device 2514 can be connected to a computer 2518 via a connection 2516. As illustrated, the connection 2516 can be a wired connection. Alternatively, the connection 2516 can be wireless.

In an alternative embodiment, the remote access device 2514 can be located at a patient's home. A patient can use the remote access device 2514 to collect data from the implanted device 2512 and forward the data to a physician via the Internet. In addition, the patient can enter additional information via the remote access device 2514 or a computer, such as observations and information about painful events. In a particular example, the remote device can connect over a wired or wireless Internet connection to transmit data to a healthcare practitioner and to receive instructions and parameters from the healthcare practitioner. The remote device 2514 can connect directly. Alternatively, the remote device 2514 can connect to a computer connected to the Internet. In either case, the remote device 2514 can access software, either embedded or at a connected computer, to permit entry of comments by the patient in addition to data received from the implanted device 2512. Furthermore, the computer connected to the device 2514 or the device 2514 itself can provide instructions to the patient. In such a manner, a remotely located healthcare practitioner can remotely monitor performance of the device, the condition of the patient, and manipulate performance of the device.

In a particular example, data retrieved from the implanted device 2512 via the remote device 2514 can be correlated with pain or sensations experienced by the patient. Such a correlation can further enhance the understanding of the healthcare provider, potentially enhancing the treatment of the patient.

CONCLUSION

With the implanted device described above, osteal structures can be fused or bone growth can be effected. In particular, such devices can be implanted using laparoscopic techniques. Such devices can further reduce the likelihood that a more invasive disc replacement implant will be used.

In a particular embodiment, the device also can provide feedback to a healthcare practitioner regarding the state of the intervertebral disc. A healthcare provider can manipulate the performance of the device to control bone growth and degradation of soft tissue, such as the intervertebral disc or zygapophyseal joint, reducing patient discomfort and patient pain or neuro-deficit.

The above-disclosed subject matter is to be considered illustrative, and not restrictive, and the appended claims are intended to cover all such modifications, enhancements, and other embodiments that fall within the true scope of the present invention. For example, it is noted that the components in the exemplary embodiments described herein as having a particular function or as being located in a particular housing are illustrative and it is noted that such components can perform additional functions or be located in different configurations. Thus, to the maximum extent allowed by law, the scope of the present invention is to be determined by the broadest permissible interpretation of the following claims and their equivalents, and shall not be restricted or limited by the foregoing detailed description.

What is claimed is:

1. A device comprising:
   a first reservoir configured to include a degradation agent;
   a second reservoir configured to include a osteogenerative agent;
   a controller configured to selectively initiate release of the degradation agent from the first reservoir and the osteogenerative agent from the second reservoir;
   a sensor in communication with the controller and configured to measure a condition of a soft tissue, wherein the controller selectively initiates access to the first reservoir or the second reservoir based at least in part on the condition measured by the sensor; and
   a housing overlying the controller and sensor and having an expandable mechanism with an expandable element for moving first and second portions between expanded and unexpanded configurations, wherein the housing has at least one dimension of less than 8 mm.

2. The device of claim 1, wherein the controller is configured to initiate release of the degradation agent prior to initiating release of the osteogenerative agent, and the expandable element comprises a balloon.

3. The device of claim 1, wherein the condition includes pressure.

4. The device of claim 1, wherein the condition includes hydration level, and further comprising a delivery instrument that moves the expandable mechanism between the expanded and unexpanded configurations.

5. The device of claim 4, further comprising a control element configured to provide access to the first reservoir, and the delivery instrument comprises a shaft with a lumen for transporting fluid relative to the expandable element.

6. The device of claim 5, wherein the controller is configured to manipulate the control element in response to a signal from a sensor, and the lumen comprises multiple lumens.

7. The device of claim 5, wherein the control element includes a valve.

8. The device of claim 5, wherein the control element includes a removable barrier.

9. The device of claim 5, wherein the control element includes a pump, and the expandable mechanism provides bi-directional expansion such that the expandable element applies a uniform expansion force between the first and second portions between leading and trailing ends thereof along a length of the expandable mechanism.

10. The device of claim 1, wherein the osteogenerative agent is an osteoinductive agent.

11. The device of claim 1, further comprising a reservoir driver configured to motivate at least one of the degradation agent to exit the first reservoir or the osteogenerative agent to exit the second reservoir.

12. An implantable medical device comprising:
a first reservoir configured to include a degradation agent;
a second reservoir configured to include a osteogenerative agent;
a controller configured to selectively initiate release of the degradation agent from the first reservoir prior to initiating release of the osteogenerative agent from the second reservoir;
a sensor in communication with the controller and configured to sense a condition of a soft tissue, wherein the controller selectively initiates access to the first reservoir or the second reservoir in response to a signal from the sensor; and
a housing overlying the controller and sensor and having an expandable mechanism having first and second portions, linkages for movably coupling the first and second portions to each other and moving the first and second portions between expanded and unexpanded configurations, wherein the housing has at least one dimension of less than 8 mm.

13. The device of claim 12, further comprising a control element configured to provide access to the first reservoir, first and second members pivotally coupled to each other with first ends positioned in respective receptacles of the first portion, and opposite second ends positioned in respective receptacles the second portion, and ends of the first and second members interdigitate with a ratchet surface formed along the respective receptacles.

14. The device of claim 13, wherein the controller is configured to manipulate the control element in response to a condition determined by a sensor.

15. The device of claim 13, further comprising a remote access component in communication with the controller, and in the unexpanded configuration, the ends of the first and second members are positioned at outer ends of the respective receptacles, the first and second portions move bi-directionally away from each other, the ends of first and second members move longitudinally toward each other along the receptacles, the first and second members move the first and second portions away from each other and engage ratchet surfaces along the receptacles to maintain the expanded or unexpanded configurations, such that the expandable mechanism is collapsible to facilitate insertion in a collapsed disc space with a delivery instrument, and thereafter expandable to distract the disc space and maintain distraction post-operatively.

16. An implantable medical device comprising:
a first reservoir configured to include a degradation agent;
a second reservoir configured to include a osteogenerative agent;
a sensor configured to sense a condition of a soft tissue;
a controller in communication with the sensor, wherein the controller selectively initiates release of the degradation agent from the first reservoir and the osteogenerative agent from the second reservoir based on a signal from the sensor; and
a housing overlying the controller and sensor and having an expandable mechanism having first and second portions with expanded and unexpanded configurations, the first and second portions having respective sidewalls, arms, receptacles formed on ends of the arms and engagement surfaces extending along the receptacles, wherein the housing has at least one dimension of less than 8 mm.

17. The device of claim 16, wherein the controller is configured to initiate release of the degradation agent prior to initiating release of the osteogenerative agent, and the arms have respective engagement surfaces that are engageable, and the engagement surfaces interdigitate and engage each other to maintain the expanded configuration.

* * * * *